United States Patent
Konh

(10) Patent No.: US 10,806,898 B2
(45) Date of Patent: Oct. 20, 2020

(54) STEERABLE SURGICAL DEVICES WITH SHAPE MEMORY ALLOY WIRES

(71) Applicant: UNIVERSITY OF HAWAII, Honolulu, HI (US)

(72) Inventor: Bardia Konh, Honolulu, HI (US)

(73) Assignee: UNIVERSITY OF HAWAII, Honolulu, HI (US)

( * ) Notice: Subject to any disclaimer, the term of this patent is extended or adjusted under 35 U.S.C. 154(b) by 35 days.

(21) Appl. No.: 16/077,394

(22) PCT Filed: Mar. 30, 2018

(86) PCT No.: PCT/US2018/025380
§ 371 (c)(1),
(2) Date: Aug. 10, 2018

(87) PCT Pub. No.: WO2018/183832
PCT Pub. Date: Oct. 4, 2018

(65) Prior Publication Data
US 2019/0374746 A1    Dec. 12, 2019

Related U.S. Application Data

(60) Provisional application No. 62/587,764, filed on Nov. 17, 2017, provisional application No. 62/479,239, filed on Mar. 30, 2017.

(51) Int. Cl.
*A61M 25/01*    (2006.01)
*A61M 25/00*    (2006.01)
(Continued)

(52) U.S. Cl.
CPC ......... *A61M 25/0147* (2013.01); *A61B 34/71* (2016.02); *A61F 2/2466* (2013.01);
(Continued)

(58) Field of Classification Search
CPC .......... A61M 25/0147; A61M 25/0158; A61M 25/0082; A61M 25/09041;
(Continued)

(56) References Cited

U.S. PATENT DOCUMENTS 5,520,678 A    5/1996 Heckele et al.
5,919,199 A *  7/1999 Mers Kelly ........ A61B 17/0469
                                        606/139
(Continued)

FOREIGN PATENT DOCUMENTS

WO    2017147041 A1    8/2017

OTHER PUBLICATIONS

Abbott, "MitraClip Transcatheter Mitral Valve Repair," Available online at: <<https://www.vascular.abbott/us/products/structural-heart/mitraclip-mitral-valve-repair.html>>, Accessed Aug. 20, 2018, 4 pages.

(Continued)

*Primary Examiner* — Laura A Bouchelle
*Assistant Examiner* — Justin L Zamory
(74) *Attorney, Agent, or Firm* — Withrow & Terranova, P.L.L.C.; Vincent K. Gustafson

(57) ABSTRACT

A steerable surgical device includes a flexible joint positioned between first and second tubular elements, with multiple shape memory alloy wire elements extending across or through the joint being circumferentially spaced relative to one another and independently actuatable to effectuate pivotal movement between the first and second tubular elements (e.g., along at least two or at least three nonparallel planes) to provide enhanced maneuverability relative to single degree of freedom steerable devices. Longitudinal guide structures (e.g., channels or bores) and/or anchor points for shape memory alloy wire elements may be (Continued)

circumferentially spaced in or on the tubular elements to receive the shape memory alloy wire elements.

34 Claims, 20 Drawing Sheets

(51) Int. Cl.
 *A61M 25/09* (2006.01)
 *A61F 2/24* (2006.01)
 *A61B 34/00* (2016.01)
(52) U.S. Cl.
 CPC .... *A61M 25/0082* (2013.01); *A61M 25/0158* (2013.01); *A61M 25/09041* (2013.01); *A61M 2025/0095* (2013.01); *A61M 2025/09116* (2013.01); *A61M 2025/09141* (2013.01); *A61M 2205/0233* (2013.01); *A61M 2205/0266* (2013.01); *A61M 2205/3368* (2013.01)
(58) Field of Classification Search
 CPC ........... A61M 2025/0095; A61M 2025/09116; A61M 2025/09141; A61M 2205/0233; A61M 2205/0266; A61M 2205/3368; A61B 34/71; A61F 2/2466
 See application file for complete search history.

(56) References Cited

U.S. PATENT DOCUMENTS

| | | | | |
|---|---|---|---|---|
| 6,068,623 | A * | 5/2000 | Zadno-Azizi | A61M 25/09 600/585 |
| 6,672,338 | B1 * | 1/2004 | Esashi | A61M 25/0138 138/119 |
| 2004/0044350 | A1 * | 3/2004 | Martin | A61B 1/0057 606/139 |
| 2004/0056751 | A1 * | 3/2004 | Park | A61B 1/0008 337/139 |
| 2005/0216033 | A1 | 9/2005 | Lee et al. | |
| 2007/0038230 | A1 * | 2/2007 | Stone | A61B 17/0482 606/139 |
| 2013/0345765 | A1 | 12/2013 | Brockman et al. | |

OTHER PUBLICATIONS

Author Unknown, "MitraClip," Ehlers Danlos "Enlaces" (Argentina) blog, Available online at: <<http://ehlersdanlos-info-mas-mi-experiencia.blogspot.com/2012/07/mitraclip.html>>, Jul. 18, 2012, Accessed Aug. 20, 2018, 11 pages (webpage translated via Google).
Ayvali, E., et al., "Towards a Discretely Actuated Steerable Cannula for Diagnostic and Therapeutic Procedures," The International Journal of Robotics Research, vol. 31, Issue 5, Apr. 2012, pp. 588-603.
Black, R. J., et al., "Characterization of optically actuated MRI-compatible active needles for medical interventions," Proceedings vol. 9058, Behavior and Mechanics of Multifunctional Materials and Composites 2014, SPIE Smart Structures and Materials + Nondestructive Evaluation and Health Monitoring, 2014, San Diego, California, USA, 8 pages.
Brinson, L. C., "One-Dimensional Constitutive Behavior of Shape Memory Alloys: Thermomechanical Derivation with Non-Constant Material Functions and Redefined Martensite Internal Variable," Journal of Intelligent Material Systems and Structures, vol. 4, Apr. 1993, pp. 229-242.
Datla, N. V., et al., "A model to predict deflection of bevel-tipped active needle advancing in soft tissue," Medical Engineering & Physics, vol. 36, No. 3, Mar. 2014, pp. 285-293.
Datla, N. V., et al., "Polyacrylamide phantom for self-actuating needle-tissue interaction studies," Medical Engineering & Physics, vol. 36, No. 1, Jan. 2014, pp. 140-145.
Deuschl, F., et al., "Critical evaluation of the MitraClip system in the management of mitral regurgitation," Vascular Health and Risk Management, vol. 12, Jan. 11, 2016, pp. 1-8.
Elahinia, M. H., et al., "Control of Shape Memory Alloy Actuators," Chapter in "Shape Memory Alloy Actuators: Design, Fabrication and Experimental Evaluation," West Sussex, UK: John Wiley and Sons, Ltd., 2016.
Honarvar, M., et al., "Study of unrecovered strain and critical stresses in one-way shape memory Nitinol," Journal of Materials Engineering and Performance, vol. 23, No. 8, Aug. 2014, pp. 2885-2893.
Konh, B., "Design and Fabrication of a MirtaClip Locator Prototype for Percutaneous Transcatheter Mitral Valve Repair System," PowerPoint Presentation, Department of Mechanical Engineering, University of Hawaii at Manoa, Apr. 2017, 8 pages.
Konh, B., et al., "Design and Fabrication of a MitraClip Locator Prototype for Percutaneous Transcatheter Mitral Valve Repair System," 2017 Design of Medical Devices Conference, Apr. 10-13, 2017, Minneapolis, Minnesota, USA, 10 pages.
Konh, B., et al., "Design and Fabrication of a Robust Active Needle using SMA Wires," Design of Medical Devices Conference, Apr. 10-13, 2017, Minneapolis, Minnesota, USA, 2 pages.
Konh, B., et al., "Design optimization study of a shape memory alloy active needle for biomedical applications," Medical Engineering & Physics, vol. 37, Issue 5, May 2015, pp. 469-477.
Konh, B., et al., "Evaluating the performance of an advanced smart needle prototype inside tissue," Proceedings vol. 10164, Active and Passive Smart Structures and Integrated Systems 2017, SPIE Smart Structures and Materials + Nondestructive Evaluation and Health Monitoring, Apr. 11, 2017, 5 pages.
Konh, B., et al., "Finite element analyses of a dual actuated prototype of a smart needle," Proceedings vol. 10164, Active and Passive Smart Structures and Integrated Systems 2017, SPIE Smart Structures and Materials + Nondestructive Evaluation and Health Monitoring, Apr. 11, 2017, pp. 1-7.
Konh, B., et al., "Simulation and experimental studies in needle-tissue interactions," Journal of Clinical Monitoring and Computing, vol. 31, No. 4, Aug. 2017, pp. 861-872.
Mayo Clinic, "Mitral valve regurgitation," Available online at: <<http://www.mayoclinic.org/diseases-conditions/mitral-valve-regurgitation/symptoms-causes/dxc-20121850>>, Last updated Apr. 13, 2018, Accessed Aug. 20, 2018, 5 pages.
Merrick, G. S., et al., "Influence of timing on the dosimetric analysis of transperineal ultrasound-guided, prostatic conformal brachytherapy," Radiation Oncology Investigations, vol. 6, No. 4, May 1, 1998, pp. 182-190.
Misra, S., et al., "Mechanics of flexible needles robotically steered through soft tissue," The International Journal of Robotics Research, vol. 29, No. 13, Nov. 2010, pp. 1640-1660.
Miyano, T., et al., "Sugar micro needles as transdermic drug delivery system," Biomedical Microdevices, vol. 7, No. 3, Sep. 2005, pp. 185-188.
Morgan, N. B., "Medical shape memory alloy applications—the market and its products," Materials Science and Engineering: A, vol. 378, Issues 1-2, Jul. 25, 2004, pp. 16-23.
Nag, S., et al., "American brachytherapy society (ABS) recommendations for transperineal permanent brachytherapy of prostate cancer," International Journal of Radiation Oncology * Biology * Physics, vol. 44, No. 4, Jul. 1999, pp. 789-799.
Nkomo, V. T., et al., "Burden of valvular heart diseases: a population-based study," Lancet, vol. 368, Sep. 16, 2006, pp. 1005-1011.
Phelan, S., et al., "Epithelial displacement during breast needle core biopsy causes diagnostic difficulties in subsequent surgical excision specimens," Journal of Clinical Pathology, vol. 60, No. 4, Apr. 2007, pp. 373-376.
Podder, T. K., et al., "A novel curvilinear approach for prostate seed implantation," Journal of Medical Physics, vol. 39, No. 4, Apr. 2012, pp. 1887-1892.
Reed, K. B. et al. "Modeling and control of needles with torsional friction," IEEE Transactions on Biomedical Engineering, vol. 56, No. 12, Dec. 2009, pp. 2905-2916.
Roesthuis, R. J., et al., "Mechanics-based model for predicting in-plane needle deflection with multiple bends," 2012 4th IEEE

(56) References Cited

OTHER PUBLICATIONS

RAS & EMBS International Conference on Biomedical Robotics and Biomechatronics, Roma, Italy, Jun. 24-27, 2012, pp. 69-74.
Ryu, S. C., "Optically Controlled Magnetic Resonance Imaging Compatible Active Needle," Dissertation submitted to the Department of Mechanical Engineering and the Committee on Graduate Studies of Stanford University in partial fulfillment of the requirements for the degree of Doctor of Philosophy, Dec. 2012, 127 pages.
Swensen, J. P., et al., "Torsional dynamics of steerable needles: Modeling and fluoroscopic guidance," IEEE Transactions on Biomedical Engineering, vol. 61, No. 11, Nov. 2014, pp. 2707-2717.
Van De Berg, N. J., et al., "Design Choices in Needle Steering—A Review," IEEE/ASME Transactions on Mechatronics, vol. 20, No. 5, Oct. 2015, pp. 2172-2183.
Volpe, A., et al., "Techniques, Safety and Accuracy of Sampling of Renal Tumors by Fine Needle Aspiration and Core Biopsy," The Journal of Urology, vol. 178, No. 2, Aug. 2007, pp. 379-386.
Youk, J. H., et al., "Analysis of false-negative results after US-guided 14-gauge core needle breast biopsy," European Radiology, vol. 20, No. 4, Oct. 28, 2009, pp. 782-789.
International Search Report and Written Opinion for International Patent Application No. PCT/US2018/025380, dated Jun. 8, 2018, 12 pages.
International Preliminary Report on Patentability for International Patent Application No. PCT/US2018/025380, dated Oct. 10, 2019, 11 pages.

\* cited by examiner

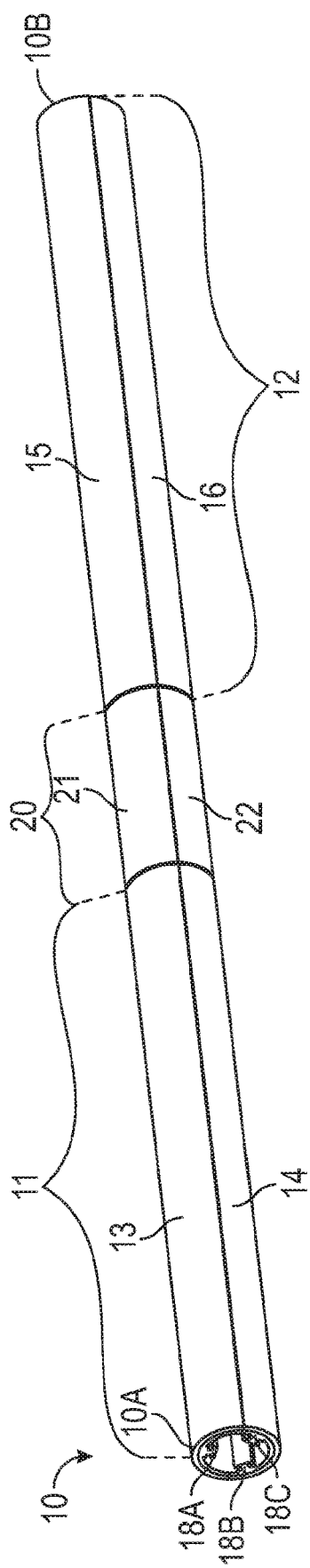
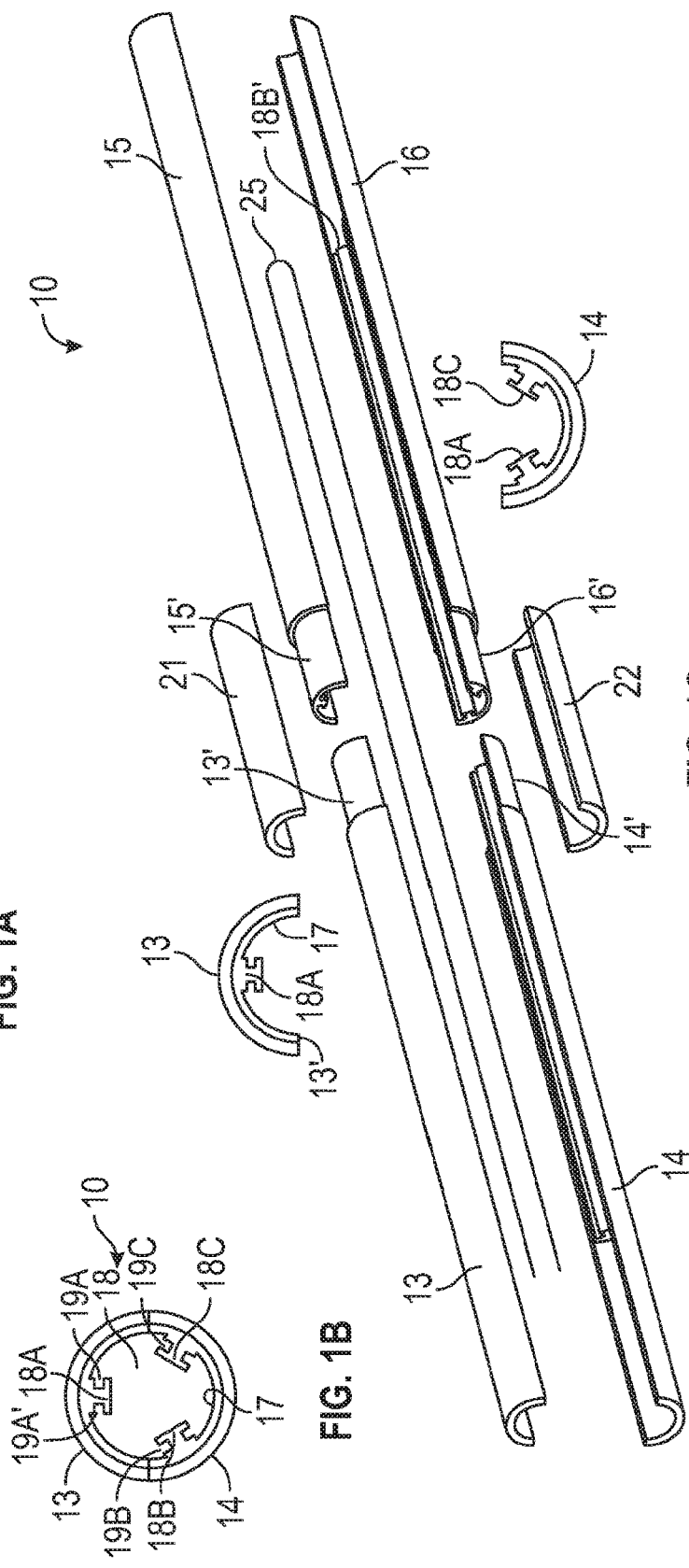
FIG. 1A
FIG. 1B
FIG. 1C

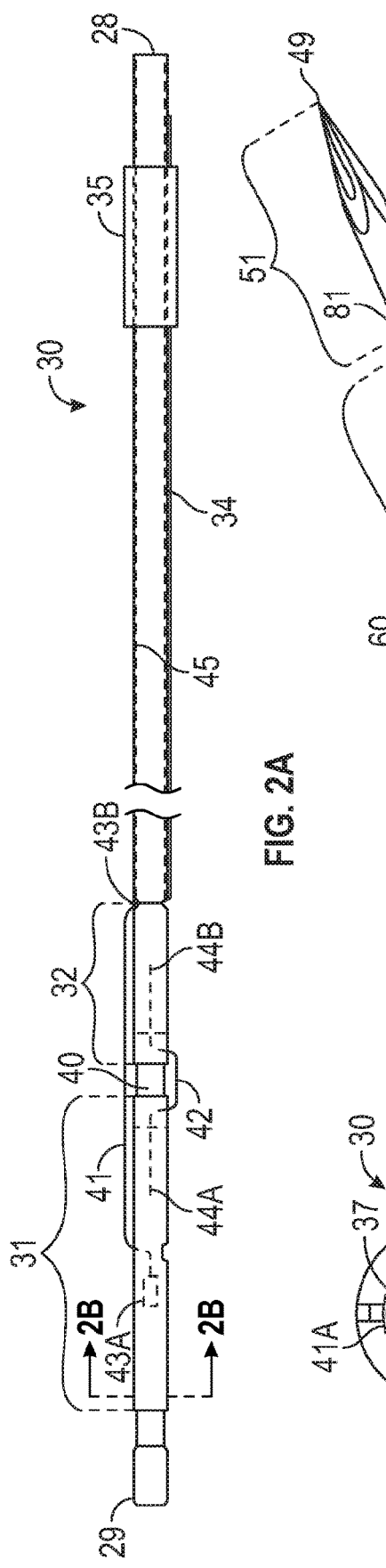
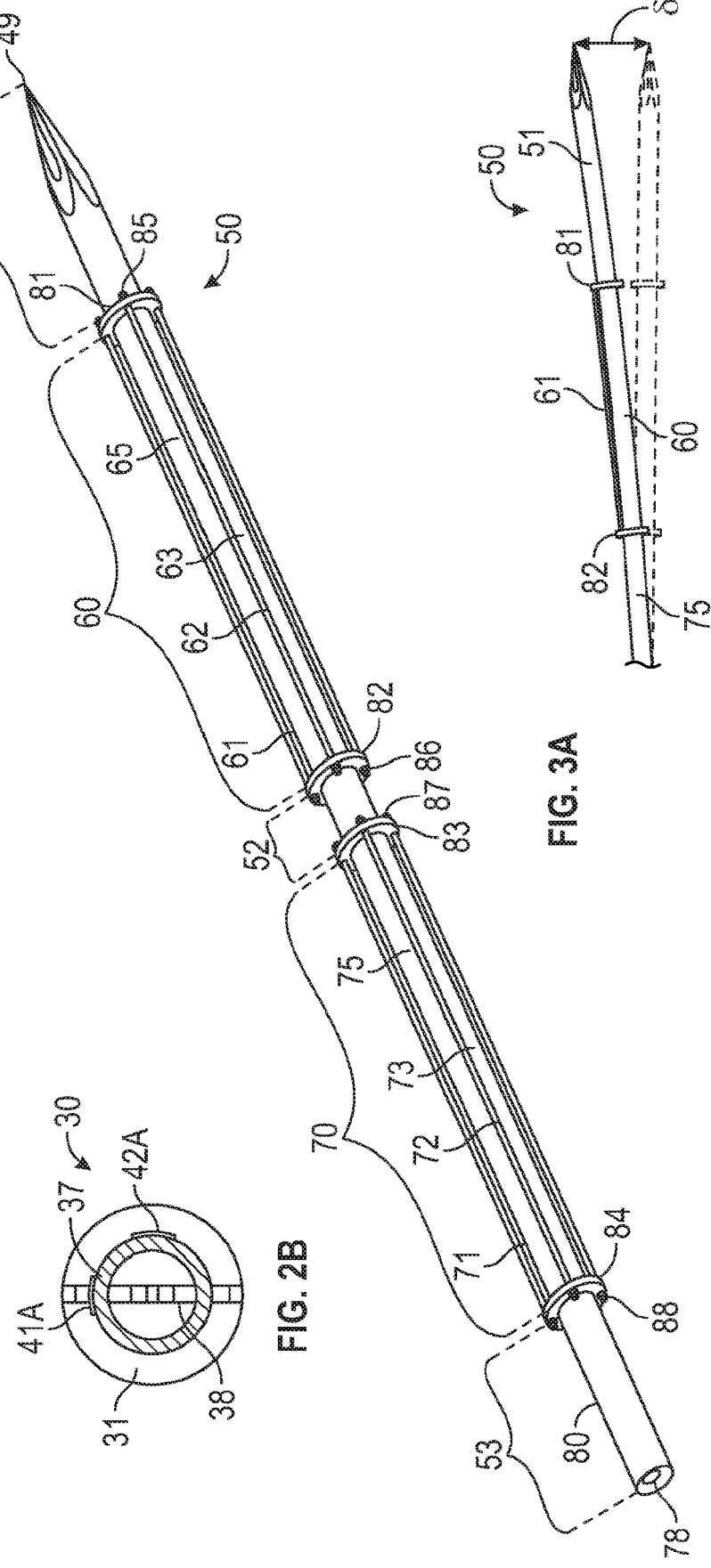
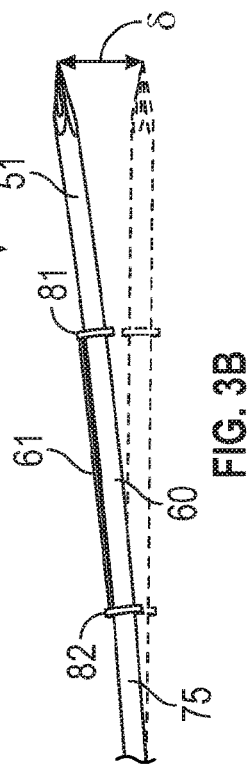

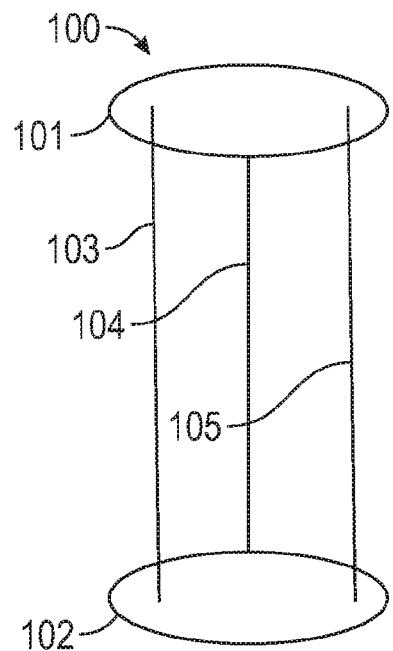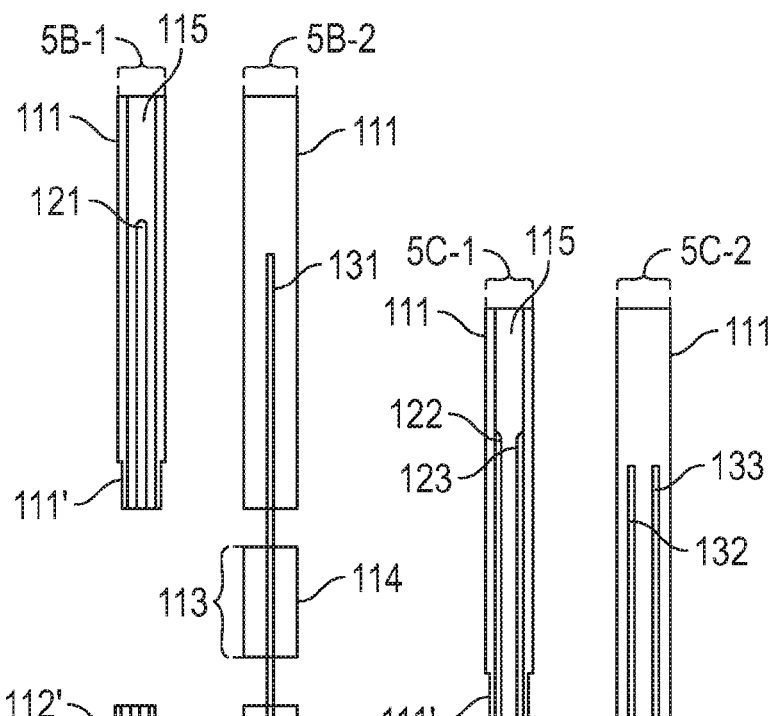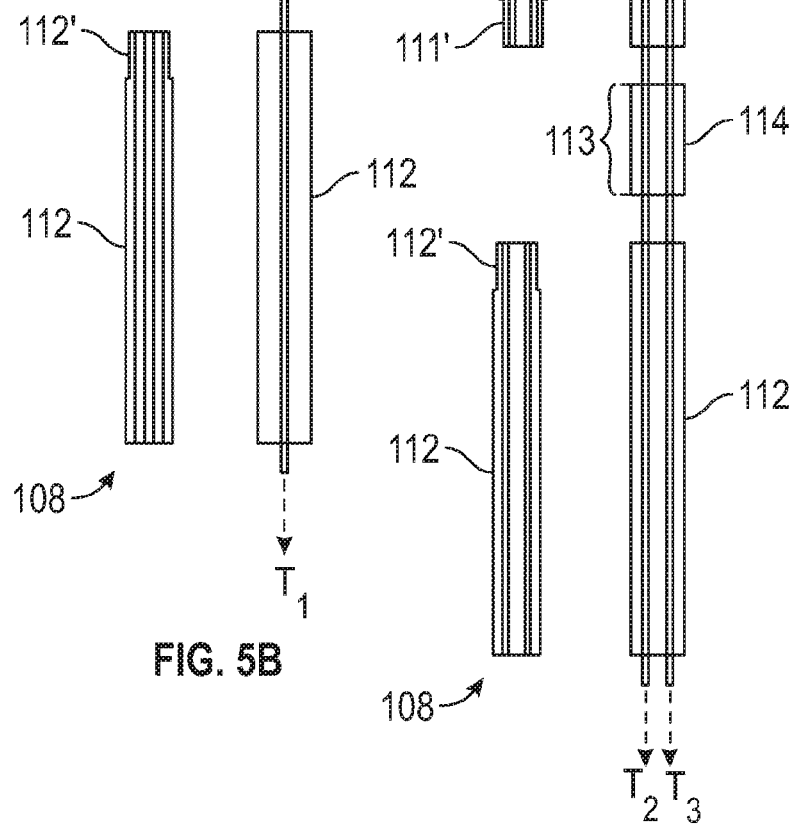

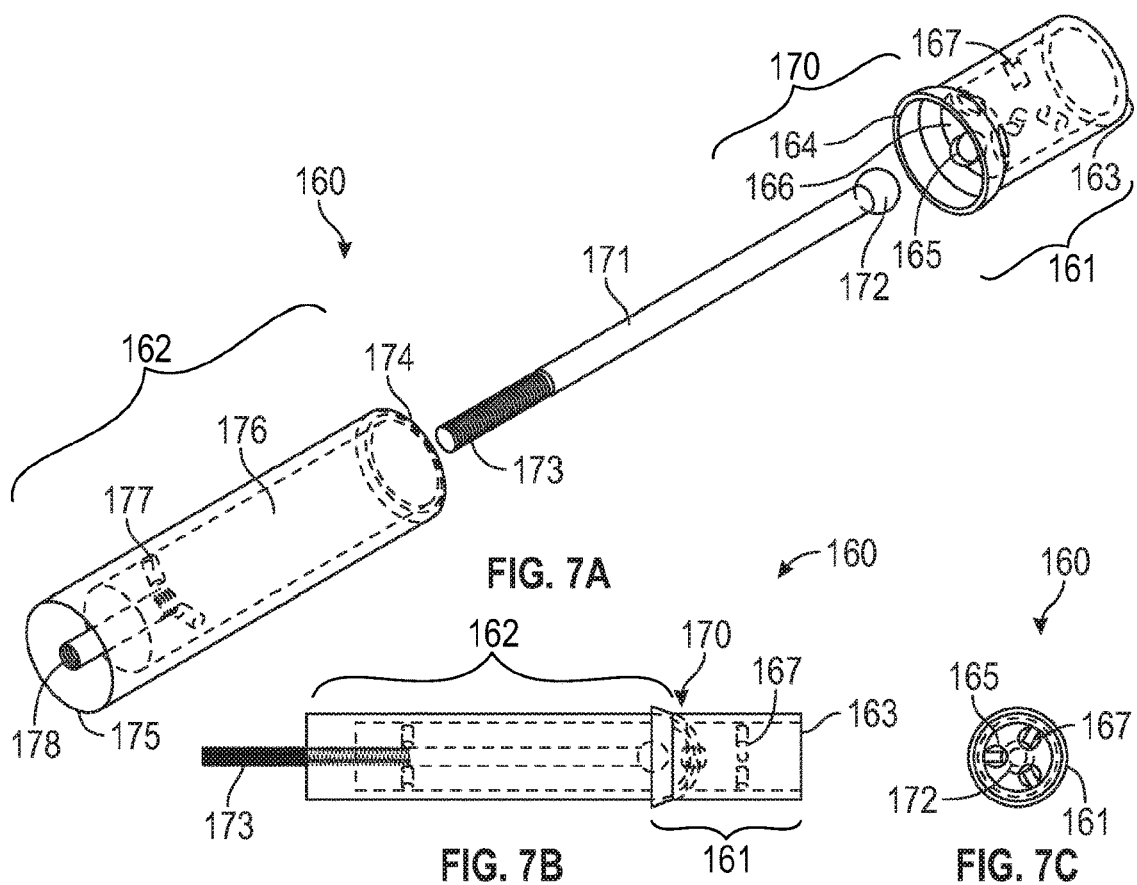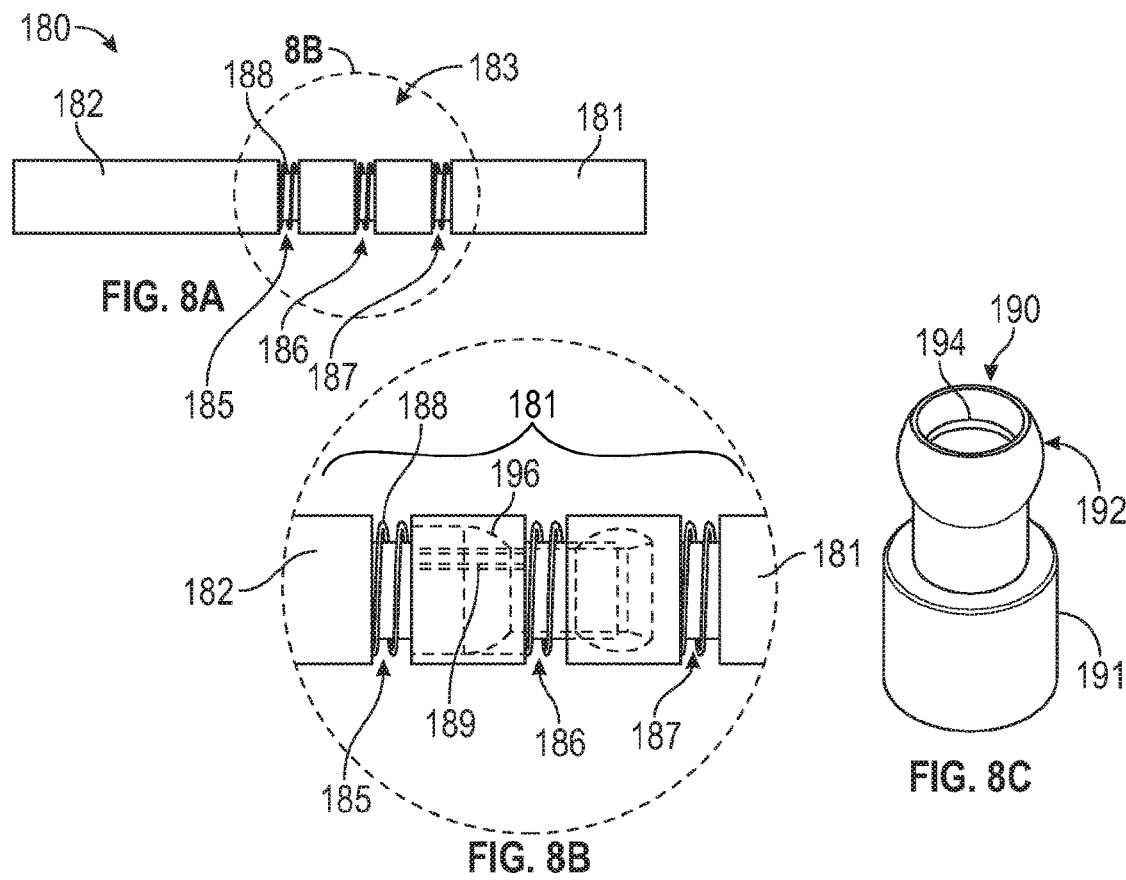

STEERABLE SURGICAL DEVICES WITH SHAPE MEMORY ALLOY WIRES

STATEMENT OF RELATED APPLICATION(S)

This application is a 35 U.S.C. § 371 national phase filing of International Application No. PCT/US2018/025380 filed Mar. 30, 2018, and claims priority to U.S. Provisional Patent Application No. 62/479,239 filed Mar. 30, 2017 and entitled "Surgical Locator Device," and to U.S. Provisional Patent Application No. 62/587,764 filed Nov. 17, 2017 and entitled "Steerable Surgical Devices with Shape Memory Alloy Wire," wherein the entire contents of the foregoing applications are hereby incorporated by reference herein.

TECHNICAL FIELD

This disclosure relates to steerable surgical devices. In particular, the present disclosure relates to steerable surgical devices utilizing multiple shape memory alloy wires.

BACKGROUND

Surgical needles are commonly used in percutaneous diagnostic and therapeutic procedures. These procedures include tissue sample removal (biopsy), internal radiotherapy (brachytherapy), and targeted drug delivery. The success of these procedures highly depends on the accuracy of needle placement at target locations. For example, malposition of the biopsy needle could result in a false diagnosis. Similarly, in brachytherapy, inaccurate positioning of the radioactive seeds could cause damage to the healthy tissue instead of attacking the cancerous cells. Currently rigid passive needles (e.g., 17 or 18 gauge needles with 2.4 mm outer diameter and 1.8 mm inner diameter, suitable for passing radioactive seeds typically about 0.8 mm in diameter) are being used in a straight path to reach the target. These needles would leave limited room for adjustment after their insertion into the patient's body. However, unpredicted factors such as human error, tissue deformation, and non-linear and nonhomogeneous properties of the tissue undermines the placement accuracy.

As an alternative to rigid passive needles, flexible steerable needles have been proposed for enhanced navigation inside patient tissues. Passive bevel-tip needles beneficially utilize unbalanced forces on their tip to create a curved path inside the tissue and reach the target. This curved path could be used to maneuver around sensitive organs during surgical intervention. However, trajectory planning with passive needles is complicated and sometimes inaccurate. With passive needles, the deflection is basically governed by needle-tissue interactions. Passive needles with a predefined shape steer in two-dimensional (2D) space with a constant radius, and thereby require axial rotation to enable maneuvering and placement in 3D space. Rotation of a needle while the needle advances through tissue is not only difficult, but also increases the risk of tissue damage.

Active needles, on the other hand, can compensate for any possible misalignments via their actuation forces. Organ movements, physiological processes such as breathing, and human errors, are typical causes for these misalignments. With the help of the active needle's actuation and control, surgeons can guide their needle through a desired trajectory with increased accuracy.

Various research studies have suggested novel designs of active needles. One example includes an active segmented cannula with multiple stainless steel rings separated by pre-curved shape memory alloy wire segments, with one SMA wire segment arranged between each pair of longitudinally segregated stainless steel rings. See Ayvali et al., Int. J. Rob. Res. 2012 April; 31(5): 588-603. Another example is disclosed by Ryu in a December 2012 Stanford University dissertation entitled "Optically Controlled Magnetic Resonance Imaging Compatible Needle" (available online at <http://purl.stanford.edu/ht443cf9111>), which provides an active needle using internal laser heating, conducted via optical fibers of a SMA actuator to produce bending in the distal section of the needle. One degree of freedom bending actuation was realized with a 1.37 mm outer diameter superelastic NiTi tube having a set of laser machined slits (rendering the tube uni-directionally flexible) and a 250 micron diameter NiTi SMA wire anchored at ends thereof to the tube by threading through two holes, to obtain localized needle tip bending.

The silent and robust actuation of SMAs, their biocompatibility, and their high power-to-mass ratio make them attractive for development of active medical devices. A key feature of SMAs is their ability to undergo a large seemingly plastic strain and subsequently recover the strain through the application of heat or load removal. The actuation behavior of SMAs is generated when an internal crystalline transformation (e.g., between Austenite (high temperature) and Martensite (low temperature) phases) happens with application of load or heat. Actuation happens when the Martensite (enlarged shape) transforms to the Austenite phase (smaller or parent shape).

Further applications for steerable surgical devices include procedures to address heart conditions. For example, mitral regurgitation (MR) is a malfunction of the mitral valve where the blood flows backward because of improper closure of the valve. The blood flows back through the mitral valve to the left atrium during the contraction of the left ventricle. This condition usually causes shortness of breath, fatigue, lightheadedness, and a rapid heartbeat. It is estimated that 2% of the global population has significant mitral valve disease, with more than 200,000 patients being diagnosed with such condition each year in the United States. Current treatments include anticoagulation medication and surgeries to replace or repair the dysfunctional mitral valve. Open heart surgery has been the conventional approach to repair or replace the mitral valve. However, for a large percentage of patients, open-heart surgery carries increased risk of mortality and morbidity due to their advanced age and dysfunction of the left ventricle. Recently, less invasive, transcatheter approaches to mitral valve disease have been developed to decrease the surgical risk for these patients.

Alternatively, a MitraClip could be used to stop or decrease the undesired leakage. MitraClip is a metal clip coated with fabric that is implanted on the mitral valve leaflets to allow the valve to close more completely. After clip placement, blood flows in an assisted fashion as the mitral valve opens and closes on the either sides of the clip. The procedure for placement of the MitraClip in Transcatheter Mitral Valve Repair (TMVR) takes 2 to 3 hours under general anesthesia. A transesophageal echocardiogram is used to observe the blood flow and to trace the placement of the clip. A catheter is guided inside the femoral artery after percutaneous access is established. Then, a guide wire is inserted to reach the mitral valve. At this time, the MitraClip is threaded into the target position between the leaflets, and finally, the guide is removed. Precise placement and orientation must be achieved to secure the clip with the minimum possible leakage. Since the implantation is being done inside a beating heart, this precise placement is particularly challenging. Currently, trial and error along with precise measurements are being utilized to find the best position. Doctors spend most of their surgical time (e.g., roughly 90 minutes) finding the correct orientation for the clip.

Other surgical procedures utilize elongated tubular bodies that are inserted into patients (e.g., for intravascular use), with such tubular bodies being embodied in catheters, cannulas, guide wires, or the like. The art continues to seek improvement in such devices to enhance their utility.

SUMMARY

Disclosed herein by way of certain exemplary embodiments is a steerable surgical device utilizing shape memory alloy wires. A steerable surgical device includes a flexible joint positioned between first and second tubular elements, with multiple shape memory alloy wire elements extending across or through the joint being independently actuatable to effectuate pivotal movement between the first and second tubular elements along multiple non-parallel planes. A shape memory alloy is an alloy that "remembers" an original state and that, following deformation, returns to its pre-deformed state when actuated (e.g., electric current, heat, magnetic field, etc.). In certain embodiments, multiple (e.g., two, three, or more) shape memory alloy wire elements are attached to circumferentially-spaced first anchor points of the first tubular element and circumferentially-spaced second anchor points of the second tubular element, and are independently actuatable to effectuate pivotal movement between the first and second tubular elements. The shape memory alloy wire elements predictably and reliably contract relative to the current transmitted therethrough. In this way, the steerable surgical device provides for precise multi-dimensional pivotal movement of the first tubular element relative to the second tubular element. For example, the presence of at least three properly configured and independently actuatable shape memory alloy wire elements may permit adjustment of pivot angles between the first tubular element and the second tubular element along at least three non-parallel planes. This exacting control and precision allows the steerable surgical device to be fed through and/or inserted into the body for a variety of medical applications.

In an exemplary aspect, the present disclosure relates to a steerable surgical device including a first tubular element, a second tubular element, a joint (e.g., at least a first joint), and a plurality of shape memory alloy wire elements. The first tubular element includes a first plurality of anchor points, and the second tubular element includes a second plurality of anchor points. The joint is arranged between the first tubular element and the second tubular element, and is configured to allow pivotal movement between the first tubular element and the second tubular element. The plurality of shape memory alloy wire elements extends across or through the first joint, is attached to the first plurality of anchor points, and is attached to the second plurality of anchor points. At least some shape memory alloy wire elements are independently actuatable to effectuate pivotal movement between the first tubular element and the second tubular element.

In certain embodiments, separate actuation of the at least some shape memory alloy wire elements is configured to permit adjustment of pivot angles between the first tubular element and the second tubular element along at least two, or at least three, non-parallel planes.

In certain embodiments, individual shape memory alloy wire elements are configured to contract responsive to application of an electrical current thereto to cause pivotal movement between the first tubular element and the second tubular element. In certain embodiments, each shape memory alloy wire element is in conductive electrical communication with at least one electrical conductor.

In certain embodiments, each shape memory alloy wire element comprises a first end in conductive electrical communication with a first electrical conductor and a second end in conductive electrical communication with a second electrical conductor.

In certain embodiments, the first plurality of anchor points is interior to the first tubular element and the second plurality of anchor points is interior to the second tubular element.

In certain embodiments, at least some (or all) shape memory alloy wire elements are pretensioned between at least some anchor points of the first plurality of anchor point and at least some anchor points of the second plurality of anchor points. In certain embodiments, each shape memory alloy wire element comprises a pretensioning stress value in a range of from about 100 MPa to about 200 Mpa. In certain embodiments, the at least one shape memory alloy wire element comprises a diameter in a range of from about 0.1 mm to about 0.2 mm.

In certain embodiments, each shape memory alloy wire element comprises a first end, a second end, a first attachment point proximate the first end, a second attachment point proximate the second end, and an intermediate point arranged between the first and second ends. The first attachment point and the second attachment point of each shape memory alloy wire element are attached to at least one first anchor point, and the intermediate point of each shape memory alloy wire element is attached to at least one second anchor point.

In certain embodiments, at least one anchor point of the first plurality of anchor points is circumferentially spaced from at least one other anchor point of the first plurality of anchor points by a distance equal to an arc length defined by a first angle of at least 90 degrees (or at least 110 degrees, or about 120 degrees) when a vertex of the first angle coincides with a center of the first tubular element, and at least one anchor point of the second plurality of anchor points is circumferentially spaced at least one other anchor point of the second plurality of anchor points by a distance equal to an arc length defined by a second angle of at least 90 degrees (or at least 110 degrees, or about 120 degrees) when a vertex of the second angle coincides with a center of the second tubular element.

In certain embodiments, the plurality of shape memory alloy wire elements comprises first, second, and third shape memory alloy wire elements, with each of the first, second, and third shape memory alloy wire elements being independently controllable and circumferentially-spaced apart from each other of the first, second, and third shape memory alloy wire elements to enable three-dimensional pivotal movement of the first tubular element relative to the second tubular element. In certain embodiments, at least portions of the first, second, and third shape memory alloy wire elements are arranged proximate to an interior surface of the first tubular element. In certain embodiments, each of the first, second, and third shape memory alloy wire elements is pretensioned. In certain embodiments, the first tubular element is biased toward a linear alignment with the second tubular element by pretensioning of the first, second, and third shape memory alloy wire elements.

In certain embodiments, at least portions of the first, second, and third shape memory alloy wire elements extend in a longitudinal direction through a wall of the first tubular element and through a wall of the second tubular element.

In certain embodiments, the first tubular element comprises a first semi-tubular portion extending in a longitudinal direction and a second semi-tubular portion extending in the longitudinal direction, with the second semi-tubular portion being configured to mate with the first semi-tubular portion. The at least one first anchor point comprises a primary anchor point positioned in the first semi-tubular portion, and comprises secondary and tertiary anchor points positioned in the second semi-tubular portion. In certain embodiments, the joint comprises a first semi-tubular joint portion and a second semi-tubular joint portion configured to mate with the first semi-tubular joint portion. In certain embodiments, the first semi-tubular portion comprises a first half-tubular portion, and the second semi-tubular portion comprises a second half-tubular portion.

In certain embodiments, the joint comprises a stiffness that is less than a stiffness of the first tubular element and less than the stiffness of the second tubular element. In certain embodiments, the joint comprises a flexible sleeve.

In certain embodiments, a third tubular element arranged between the first tubular element and the joint (i.e., embodying a first joint); and a second joint arranged between, and configured to allow pivotal movement between, the first tubular element and the third tubular element. The plurality of shape memory alloy wire elements extend across or through the third joint. At least some shape memory alloy wire elements of the plurality of shape memory alloy wire elements are independently actuatable to effectuate pivotal movement between the first tubular element and the second tubular element, and pivotal movement between the first tubular element and the third tubular element In certain embodiments, each of the first tubular element and the second tubular element comprises a plurality of longitudinal guide structures each configured to receive at least one shape memory alloy wire element of the plurality of shape memory alloy wire elements. In certain embodiments, each longitudinal guide structure of the plurality of longitudinal guide structures comprises a guide body defining at least one longitudinal slot arranged proximate to an internal wall of either the first tubular element or the second tubular element. In certain embodiments, each longitudinal guide structure of the plurality of longitudinal guide structures defines a longitudinal bore defined in a wall of either the first tubular element or the second tubular element.

In certain embodiments, an anchor point of the first plurality of anchor points is arranged proximate to one end of each longitudinal guide structure, an anchor point of the second plurality of anchor points is arranged proximate to an opposing end of each longitudinal guide structure, and each shape memory alloy wire element is configured for slidable movement within a different longitudinal guide structure of the plurality of longitudinal guide structures.

In certain embodiments, the first tubular element comprises a needle tip.

In certain embodiments, the steerable surgical device comprises at least one of a catheter, a cannula, or a guidewire.

In certain embodiments, the at least one shape memory alloy wire element comprises a thermally responsive shape memory alloy wire element.

In certain embodiments, the steerable surgical device is configured for positioning and deployment of an implantable mitral valve repair device.

In another exemplary aspect, the present disclosure relates to a steerable surgical device including a first tubular element comprising a first plurality of anchor points, a second tubular element comprising a second plurality of anchor points, and a first joint arranged between, and configured to allow pivotal movement between, the first tubular element and the second tubular element. The device further includes a plurality of shape memory alloy wire elements extending across or through the first joint, attached to the first plurality of anchor points, and attached to the second plurality of anchor points. At least some shape memory alloy wire elements of the plurality of shape memory alloy wire elements are independently actuatable to effectuate pivotal movement between the first tubular element and the second tubular element. Separate actuation of the at least some shape memory alloy wire elements is configured to permit adjustment of pivot angles between the first tubular element and the second tubular element along at least two non-parallel planes.

In another exemplary aspect, the present disclosure relates to a steerable surgical device including a first tubular element comprising a first plurality of anchor points, a second tubular element comprising a second plurality of anchor points, a joint arranged between and configured to allow pivotal movement between the first and second tubular elements, and a plurality of shape memory alloy wire elements. The plurality of shape memory wire elements extend through the first plurality of longitudinal guide structures, extending across or through the first joint, extending through the second plurality of longitudinal guide structures, attached to the first plurality of anchor points, and attached to the second plurality of anchor points. At least some shape memory alloy wire elements of the plurality of shape memory alloy wire elements are independently actuatable to effectuate pivotal movement between the first tubular element and the second tubular element. Separate actuation of the at least some shape memory alloy wire elements configured to permit adjustment of pivot angle between the first tubular element and the second tubular element along at least two non-parallel planes.

In another exemplary aspect, the present disclosure relates to a steerable surgical device comprising a first tubular element comprising a first plurality of anchor points and a first plurality of longitudinal guide structures, a second tubular element comprising a second plurality of anchor points and a second plurality of longitudinal guide structures, a joint arranged between and configured to allow pivotal movement between the first tubular element and the second tubular element, and a plurality of shape memory alloy wire elements. At least one longitudinal guide structure of the first plurality of longitudinal guide structures is circumferentially spaced from at least one other longitudinal guide structure of the first plurality of longitudinal guide structures. At least one longitudinal guide structure of the second plurality of longitudinal guide structures is circumferentially spaced from at least one other longitudinal guide structure of the second plurality of longitudinal guide structures. The shape memory alloy wire elements extend through the first plurality of longitudinal guide structures, extend across or through the first joint, extending through the second plurality of longitudinal guide structures, are attached to the first plurality of anchor points, and are attached to the second plurality of anchor points. At least some shape memory alloy wire elements of the plurality of shape memory alloy wire elements are independently actuatable to effectuate pivotal movement between the first tubular element and the second tubular element.

In certain embodiments, separate actuation of the at least some shape memory alloy wire elements is configured to permit adjustment of pivot angle between the first tubular element and the second tubular element along at least two non-parallel planes. In certain embodiments, the joint comprises silicone.

In another exemplary aspect, the present disclosure relates to a steerable surgical device comprising a plurality of tubular elements (including first, second, and third tubular elements), a plurality of joints, and a plurality of shape memory alloy wire. Each tubular element of the plurality of tubular elements comprises a plurality of longitudinal guide structures. The plurality of joints includes a first joint arranged between and configured to permit pivotal movement between the first tubular element and the second tubular element, and includes a second joint arranged between and configured to permit pivotal movement between the second tubular element and the third tubular element. The plurality of shape memory alloy wire elements extend through the plurality of longitudinal guide structures of the first, second, and third tubular elements, and extend across or through the first joint and the second joint. At least some shape memory alloy wire elements of the plurality of shape memory alloy wire elements are independently actuatable to effectuate pivotal movement (i) between the first tubular element and the second tubular element and (ii) between the second tubular element and the third tubular element.

In certain embodiments, each longitudinal guide structure of the plurality of longitudinal guide structures comprises a longitudinal bore defined in a wall of the first tubular element, the second tubular element, or the third tubular element. In certain embodiments, each longitudinal guide structure of the plurality of longitudinal guide structures comprises a guide body defining at least one longitudinal slot arranged proximate to an internal wall of the first tubular element, the second tubular element, or the third tubular element.

In certain embodiments, the plurality of shape memory alloy wire elements comprises first, second, and third shape memory alloy wire elements, with each of the first, second, and third shape memory alloy wire elements being independently controllable and circumferentially spaced apart from each other of the first, second, and third shape memory alloy wire elements to enable three-dimensional pivotal movement of at least one of (i) the first tubular element relative to the second tubular element, or (ii) the second tubular element relative to the third tubular element.

In certain embodiments, each of the first, second, and third shape memory alloy wire elements is pretensioned. In certain embodiments, the first, second, and third tubular elements are biased toward linear alignment with one another by pretensioning of the first, second, and third shape memory alloy wire elements.

In certain embodiments, each joint of the plurality of joints comprises a flexible sleeve having a larger diameter than a diameter of each of the first tubular element, the second tubular element, and the third tubular element. In certain embodiments, at least one tubular element of the plurality of tubular elements comprises a plurality of anchor points, including anchor points circumferentially spaced from one another.

In another aspect, any one or more aspects or features described herein may be combined with any one or more other aspects or features for additional advantage.

Other aspects and embodiments will be apparent from the detailed description and accompanying drawings.

Those skilled in the art will appreciate the scope of the present disclosure and realize additional aspects thereof after reading the following detailed description of the certain exemplary embodiments in association with the accompanying drawing figures.

BRIEF DESCRIPTION OF DRAWINGS

FIG. 1A is a perspective view of at least a portion of a first steerable surgical device according to an embodiment of the present disclosure including a flexible joint positioned between first and second tubular elements each including first through third anchor points arranged on inner surfaces thereof for receiving shape memory alloy elements that extend through the flexible joint.

FIG. 1B is a cross-sectional view of the steerable surgical device of FIG. 1A showing first through third anchor points arranged on inner surfaces of a tubular element.

FIG. 1C is an exploded perspective view of the steerable surgical device of FIGS. 1A and 1B.

FIG. 2A is a side elevation view of a second steerable surgical device (for mitral valve placement) according to an embodiment of the present disclosure.

FIG. 2B is a cross-sectional view of the steerable surgical device of FIG. 2A.

FIG. 3A is a side elevation view of a third steerable surgical device according to an embodiment of the present disclosure.

FIG. 3B is a side elevation view of the steerable surgical device of FIG. 3A in a deflected state, superimposed over a dashed line representation of the steerable surgical device in a straight or undeflected state.

FIG. 5A is a simplified schematic view of two disc-shaped surfaces interconnected by three generally parallel wires in a pretensioned state and arranged approximately 120 degrees apart from one another.

FIG. 5B includes a first frame providing a cross-sectional view of two tubular elements showing a first anchor within a first tubular element of a steerable surgical device, and includes a second frame providing a schematic view of a first shape memory alloy wire affixed to the first anchor and subjected to a pretensioning step.

FIG. 5C includes a first frame providing a cross-sectional view of the tubular elements of FIG. 5B showing second and third anchors within the distal tubular element of the steerable surgical device, and includes a second frame providing a schematic view of second and third shape memory alloy wires affixed to the second and third anchors, respectively, and subjected to a pretensioning step.

FIG. 7A is an exploded perspective view of a steerable surgical device according to another embodiment of the present disclosure, including an internal rod having one threaded end and one ball-defining end arrangeable between two tubular elements, with internal structures of the two tubular elements shown in dashed lines.

FIG. 7B is a side elevation view of the steerable surgical device of FIG. 7A in an assembled state, with internal structures of the two tubular elements shown in dashed lines.

FIG. 7C is a cross-sectional view of a portion of the steerable surgical device of FIGS. 7A and 7B.

FIG. 8A is a side elevation view of a steerable surgical device including a multi-segment joint and inter-segment tensioning springs according to another embodiment of the present disclosure.

FIG. 8B is a magnified side elevation view of a central portion of the steerable surgical device of FIG. 8A, with internal structures shown in dashed lines.

FIG. 8C is a perspective view of a joint-forming element of the steerable surgical device of FIGS. 8A and 8B.

DETAILED DESCRIPTION

Figure 4:
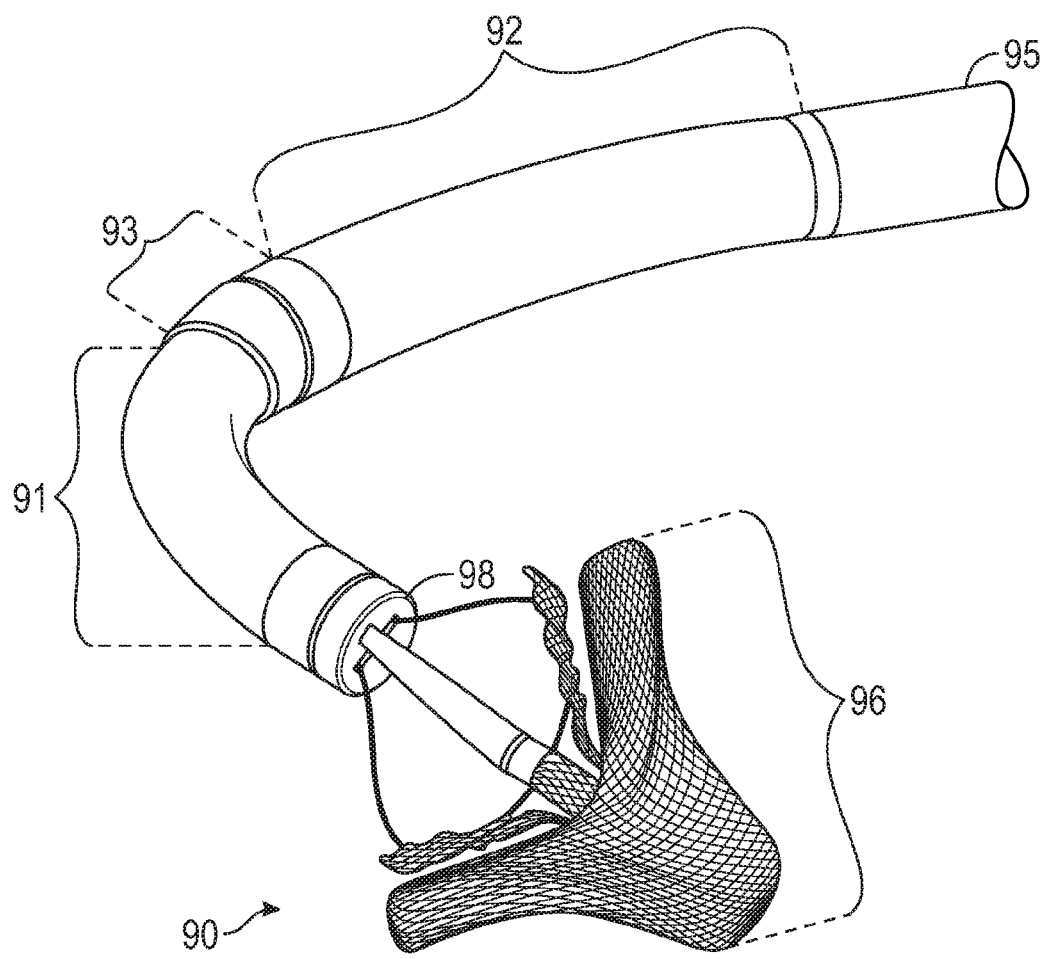
FIG. 4 is a perspective view of a steerable surgical device with a MitraClip device, prior to percutaneous insertion.

The exemplary embodiments set forth below represent the necessary information to enable those skilled in the art to practice the embodiments and illustrate the best mode of practicing the embodiments. Upon reading the following description in light of the accompanying drawing figures, those skilled in the art will understand the concepts of the disclosure and will recognize applications of these concepts not particularly addressed herein. It should be understood that these concepts and applications fall within the scope of the disclosure and the accompanying claims.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present disclosure. As used herein, the term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Relative terms such as "below" or "above" or "upper" or "lower" or "horizontal" or "vertical" may be used herein to describe a relationship of one element, layer, or region to another element, layer, or region as illustrated in the Figures. It will be understood that these terms and those discussed above are intended to encompass different orientations of the device in addition to the orientation depicted in the Figures.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. It will be further understood that the terms "comprises," "comprising," "includes," and/or "including" when used herein specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

Disclosed herein is a steerable surgical device utilizing multiple shape memory alloy wires. An exemplary steerable surgical device includes a first tubular element, a second tubular element, a flexible joint positioned therebetween, and at least one shape memory alloy wire element. In certain embodiments, the first and second tubular elements may alternatively be hollow or semi-hollow bodies having cross-sectional shapes that are round, triangular, square, rectangular, hexagonal, or embody other polygonal geometries. In certain embodiments, at least three shape memory alloy wire elements are attached to circumferentially-spaced first anchor points of the first tubular element and circumferentially-spaced second anchor points of the second tubular element. The flexible joint attaches the first and second tubular elements with each of the three shape memory alloy wire elements extending across or through the flexible joint. The shape memory alloy wire elements predictably and reliably contract upon actuation (e.g., electric current, heat, magnetic field, etc.). In particular, in certain embodiments, the shape memory alloy wire elements predictably and reliably contract relative to the current transmitted therethrough, and the flexible joint is configured to allow relative rotational movement therebetween. In this way, the steerable surgical device provides for precise three-dimensional rotational movement of the first tubular element relative to the second tubular element. This exacting control and precision allows the steerable surgical device to be fed through and/or inserted into the body for a variety of medical applications.

FIGS. 1A-1C illustrate a steerable surgical device 10 according to one embodiment. The steerable surgical device 10 includes a first tubular element 11 (which may also be referred to as a proximal tubular element), a second tubular element 12 (which may also be referred to as a distal tubular element), a joint 20 (which may also be referred to as a flexible joint, sleeve, etc.) arranged between the first tubular element 11 and the second tubular element 12, and at least one shape memory alloy wire element 25 (shown in FIG. 1C) extending through the joint 20. The first tubular element 11 includes a first group of anchor points (embodying ends of longitudinal guide elements 18A-18C) and the second tubular element includes a plurality of second anchor points (including and end of anchor point 18B' shown in FIG. 1C). Each longitudinal guide element 18A-18C is configured to receive one or more shape memory alloy wire elements and guide sliding movement of the one or more shape memory alloy wire elements therein. In certain embodiments, each longitudinal guide element 18A-18C may be formed by extrusion, either concurrently with formation of semi-tubular portions 13, 14, or in the form of inserts 13', 14' that may be affixed to the semi-tubular portions 13, 14. (Inserts 15', 16' may similarly be provided along an interior of the semi-tubular portions 15, 16 of the second tubular element 12. In certain embodiments, at least three shape memory alloy wire elements 25 are attached to circumferentially-spaced anchor points 18A-18C of the first tubular element 11 and circumferentially-spaced anchor points (e.g., 18B') of the second tubular element 12. The anchor points 18A-18C are evenly distributed about a circumference of the first tubular element 11; accordingly, they are circumferentially spaced apart from one another by a distance equal to an arc length defined by an angle of 120 degrees when a vertex of the angle coincides with a center of the first tubular element 11. The flexible joint 20 attaches the first tubular element 11 to the second tubular element 12 with each of the three shape memory alloy wire elements 25 extending across the flexible joint 20. The shape memory alloy wire elements 25 are independently controllable, and are capable of predictably and reliably contracting responsive to application of electric current (e.g., as might be delivered in a computer-controlled, programmed, or sequential manner in certain embodiments), and the flexible joint 20 is configured to allow pivotal movement between the first and second tubular elements 11, 12 coupled thereto. In this manner, the steerable surgical device 10 provides for precise three-dimensional pivotal movement of the first tubular element 10 relative to the second tubular element 11, by independent actuation of the shape memory alloy wire elements 25. This exacting control and precision allows the steerable surgical device to be fed through and/or inserted into the body for a variety of medical applications including, but not limited to, locating, positioning, and/or deploying a MitraClip for percutaneous transcathether mitral valve repair).

The steerable surgical device 10 includes a first end 10A and a second end 10B opposite the first end. The steerable surgical device 10 could include one or more of a catheter, a cannula, a guidewire, or other surgical devices recognized as suitable by those of ordinary skill in the art. In certain embodiments, a steerable surgical device is configured for positioning and deployment of an implantable mitral valve repair device. In certain embodiments, the first tubular element 10 comprises a needle tip (not shown) for insertion of the steerable surgical device 10 into an organ or other body part.

With continued reference to FIGS. 1A-1C, the first tubular element 11 includes first and second semi-tubular portions 13, 14 extending in a longitudinal direction configured to mate with one another. In certain embodiments, the first and second semi-tubular portions 13, 14 comprise half-tubular portions. However, in other embodiments, a first tubular element may embody a single tubular portion (i.e., arranged as a hollow cylinder), or may include more than two semi-tubular portions.

The first tubular element 10 further includes a plurality of first longitudinal guide elements 18A-18C positioned at an interior surface 17 of the first tubular element 10. Each first longitudinal guide element 18A-18C is generally shaped similar to an I-beam or a T-beam. In other words, each first longitudinal guide element 18A-18C defines first and second opposing longitudinal channels or slots 19A-19C, which are each configured to receive a shape memory alloy wire element 25. Although each longitudinal guide element 18A-18C as illustrated defines two longitudinal channels or slots 19A-19C, it is to be appreciated that in certain embodiments a guide element may include any suitable number of one or more channels, slots, or bores to receive one, two, three, or more shape memory alloy wire elements (or segments thereof if a first segment of a shape memory alloy wire element is fed in a first direction through a guide element, with an intermediate point of shape memory alloy wire element being attached (e.g., looped, crimped, adhered, etc.) to an anchor, and with a second segment of the same shape memory alloy wire element being fed back through the same guide element in a second direction opposing the first direction). Multiple shape memory alloy wire elements (and/or multiple parallel segments thereof) may beneficially be used to generate higher bending forces in case needle-based procedures are to be performed in relatively stiff body tissues. One or more ends of each first longitudinal guide element 18A-18C defines the anchor points.

The plurality of first longitudinal guide bodies includes a primary longitudinal guide element 18A, a secondary longitudinal guide element 18B, and a tertiary longitudinal guide element 18C, which are circumferentially spaced relative to one another. The plurality of first anchor points includes a primary anchor point, a secondary anchor point, and a tertiary anchor point circumferentially-spaced around an interior of the first tubular element. In particular, the primary longitudinal guide body 18A defines the primary anchor point, the secondary longitudinal guide body 18B defines the secondary anchor point, and the tertiary longitudinal guide body 18C defines the tertiary anchor point. In certain embodiments, the primary anchor point 18A is positioned at an internal surface 17 of the first semi-tubular portion 13, and the secondary and tertiary anchor points 18B, 18C are positioned at an internal surface 17 of the second semi-tubular portion 14.

In a manner similar to the first tubular element 11, the second tubular element 12 includes first and second semi-tubular portions 15, 16 each extending in a longitudinal direction and configured to mate with one another. In the same manner as the first tubular element 11, the second tubular element 12 includes a plurality of second longitudinal guide elements (e.g., 18B') positioned at an interior surface of the second tubular element 12, with details thereof being the same as the corresponding elements of the first tubular element 12.

The joint 20 (which may also be embodied in or include a sleeve) may be one unitary body in certain embodiments, or in other embodiments may include first and second semi-tubular portions 21, 22 each extending in a longitudinal direction and configured to mate with one another.

In certain embodiments, the joint 20 includes first and second ends each defining an opening. At least a portion of the first tubular element 11 may be positioned within the first opening of the joint 20, and at least a portion of the second tubular element 12 positioned within the second opening of the joint 20, with a gap between the first and second tubular elements 11, 12. In other embodiments, the joint 20 may be positioned within an interior of the first and/or second tubular elements 11, 12.

The joint 20 has a stiffness that is less than a stiffness of each of the first and second tubular elements 11, 12. Accordingly, the flexibility of the joint 20 (relative to the first and second tubular elements 11, 12) allows the first tubular element 11 to pivot relative to the second tubular element 12, particularly when subjected to a bending force by actuation of the shape memory alloy wires 25. In certain embodiments, the joint 20 includes a polymeric (e.g., Viton fluoroelastomer) tube, which may be opaque in appearance. In certain embodiments, other flexible materials may be used (e.g., flexible biocompatible materials).

The plurality of shape memory alloy wire elements 25 could include Nitinol (TiNi) and/or another shape memory alloy material. To obtain desired performance, the plurality of shape memory alloy wire elements 25 may be trained. For example, in certain embodiments, Nitinol wires may be trained by applying 80 cycles of heating and cooling to the wires under a certain level of stress. Then, initial tension of the wires may be set accurately upon attachment to a joint of a steerable surgical device. In other words, shape memory alloy wire elements should be under a certain stress level while the steerable surgical device is in its straight initial shape. This amount of initial stress may be set by pulling the wires (discussed in more detail below). This initial stress will assure the wire to be in the Martensite determined phase (largest crystallographic shape) prior to actuation. At this point, by applying heat to the wires by resistance heating upon electrification with the attached electrical wires, the actuation will be achieved. Applying heat will transform the wires to the Austenite phase (smallest crystallographic shape), thereby causing actuation.

In certain embodiments, a plurality of shape memory alloy wire elements 25 includes a first, second, and third shape memory alloy wire element, with each shape memory alloy wire element being independently controllable and being circumferentially spaced apart from each other shape memory alloy wire element. Utilization of multiple shape memory alloy wire elements 25 in such configuration across a joint 20 enables three-dimensional pivotal movement of a first tubular element 10 relative to a second tubular element 11. At least portions of the shape memory alloy wire elements 25 are arranged proximate to an interior surface 17 of the first and/or second tubular elements 11, 12. In certain embodiments, the shape memory alloy wire elements 25 may be positioned within and/or external to the first and/or second tubular elements 11, 12. The shape memory alloy wire elements provide a great degree of reliability, predictability, and precision, as discussed below in more detail.

Each shape memory alloy wire element comprises a first end and a second end. In certain embodiments, the at least one shape memory alloy wire element comprises a first attachment point proximate the first end, a second attachment point proximate the second end, and an intermediate attachment point therebetween. In certain embodiments, the first attachment point and the second attachment point are attached (e.g., adhered) to the first anchor point of the first tubular element, and the intermediate attachment point is attached (e.g., adhered) to the second anchor point of the second tubular element. In such an embodiment, the at least one shape memory alloy wire 25 element extends from the first anchor point of the first tubular element 11, through a first slot 19A of the first longitudinal guide element 18A of the first tubular element 11, through the joint 20, through a first slot of the second longitudinal guide element (not shown) of the second tubular element 12, loops around the second anchor point of the second tubular element 12, through a second slot of the second longitudinal guide body of the second tubular element 12, through the joint 20, through the second slot 19A' of the first longitudinal guide body 18A of the first tubular element 11, to the first anchor point. In such an embodiment, the second tubular element 12 may be positioned closer to a steerable tip of the steerable surgical device 30 than the first tubular element 11.

In certain embodiments, each shape memory alloy wire element 25 is anchored at the first and second anchor points, and is unattached within the slots (e.g., 19A-19C, 19A', etc.)

of the first and second longitudinal guide elements 18A-18C. In certain embodiments, the shape memory alloy wire elements 25 are pretensioned between the at least one first anchor point and the at least one second anchor point. In certain embodiments, the shape memory alloy wire elements 25 have a pretensioning stress value in a range of from about 100 MPa to about 200 Mpa (e.g., 150 MPa). In certain embodiments, the shape memory alloy wire elements 25 include a diameter in a range of from about 0.1 mm to about 0.2 mm.

In certain embodiments, shape memory alloy wire elements 25 are configured to contract responsive to application of an electrical current thereto (e.g., for resistive heating) and/or thermal energy, and therefore embody thermally responsive shape memory alloy wire elements. In certain embodiments, contraction of one of the shape memory alloy wire elements 25 urges the primary anchor point of the first tubular element 11 towards the second anchor point of the second tubular element 12 (due to the pretensioning of the shape memory alloy wire elements). This causes pivotal movement between the first and second tubular elements 11, 12, thereby allowing steering of the first end 10A or second end 10B of the steerable surgical device 10. For example, the primary first shape memory alloy wire element 25 may contract to pivot the first tubular element 11 relative to the second tubular element 12 at an angled (e.g., non-collinear) orientation. The secondary and tertiary shape memory alloy wire elements 25 may then contract to pivot the first tubular element 11 relative to the second tubular element 12 to another(e.g., linearly aligned) orientation.

In certain embodiments, a joint 20 may be biased towards a linear orientation, such that after cessation of application of current to the shape memory alloy wire elements 25, the first tubular element 11 returns to an orientation substantially collinear with to the second tubular element 12. Additionally, or alternatively, one or more biasing elements may be used. For example, a helical spring or torsion spring may be positioned within the joint 20.

The length of a shape memory alloy wire element 25 dictates the length of contraction of the shape memory alloy wire element 25 (e.g., 20 cm of wire will lead to 0.5 cm contraction), and accordingly the degree of pivotal movement that may be attained between the first tubular element 11 and the second tubular element 12. In certain embodiments, the shape memory alloy wire element 25 loops around the second anchor point to double the amount of force applied between the primary first anchor point and the primary second anchor point. Further, looping the shape memory alloy wire element 25 provides the first and second ends of the shape memory alloy wire element at a proximal end of the steerable surgical device (e.g., outside a patient), which makes it easier to connect ends of the shape memory alloy wire element 25 to a signal generator (e.g., electrical current generating device). In certain embodiments, a shape memory alloy wire element is in conductive electrical communication with at least one electrical conductor. In certain embodiments, the first end of the shape memory alloy wire element is in conductive electrical communication with a first electrical conductor and the second end is in conductive electrical communication with a second electrical conductor.

In certain embodiments, at least one first anchor point is arranged proximate to one end of each longitudinal guide element 18A-18C, at least one second anchor point is arranged proximate to an opposing end of each longitudinal guide element 18A-18C, and each shape memory alloy wire element 25 is configured for slidable movement within a different longitudinal groove 19A-19C.

FIG. 2A is a side elevation view of a steerable surgical device 30 for mitral valve clip placement. The steerable surgical device 30 includes a first tubular element 31 having a tip 29 for mounting a mitral valve treatment device (e.g., a MitraClip treatment clip), a joint 40, and a second tubular element 32. In certain embodiments, the joint 40 includes a shape memory polymer material. At least one shape memory alloy wire element 41 extends between the first and second tubular elements 31, 32 and across the joint 40, with ends of shape memory alloy wire element being affixed to anchors 43A, 43C. The steerable surgical device 30 further includes a torsion spring 42 to bias the first and second tubular elements 31, 32 toward a linear alignment, such as to promote recovery of an initial shape after actuation of the at least one shape memory alloy wire element 41. Electrical conductors 45 may be supplied through a hollow body 34 of the steerable surgical device 30, wherein the hollow body 34 may include any desirable sensor, mechanical retention, or mechanical release elements 35 along its length (between the first end 29 and a second end 28), optionally in electrical or sensory communication with the least one shape memory alloy wire element 41. Although only a single shape memory alloy wire element 41 is illustrated in FIG. 2A, it is to be appreciated that multiple shape memory alloy wire elements circumferentially spaced from one another and independently controllable relative to one another may be provided in certain embodiments. Further, although only a single joint 40 is shown in FIG. 2A, it is to be appreciated that multiple joints arranged in sequential fashion and each actuatable with shape memory alloy wire elements may be provided. FIG. 2B is a cross-sectional view of the steerable surgical device 30 of FIG. 2A, showing the first tubular element 31 as embodying an outer structure with an inner tube 37 and at least one functional element 38 (e.g., mechanical release structure for deployment of a MitraClip device) contained therein, and with flattened ends 41A, 42A of the at least one shape memory alloy wire element 41 and of the torsion spring 42, respectively, being retained between the inner tube 37 and the outer structure of the first tubular element 31.

FIG. 3A is a perspective view of a steerable surgical device 50 according to certain embodiments, with external shape memory alloy wire elements 61-63, 71-73. The steerable surgical device 50 includes a first tubular element 51 (including a needle point 49) and a second tubular element 52 connected by a first joint 60 that includes a first flexible core 65 with multiple shape memory alloy wire elements 61-63 (each longitudinally extending and circumferentially spaced) arranged external to the first flexible core 65. The steerable surgical device 50 further includes a third tubular element 53 and a second joint 70 spanning between the second tubular element 52 and the third tubular element 53. The second joint 70 includes a second flexible core 75 with multiple shape memory alloy wire elements 71-73 (each longitudinally extending and circumferentially spaced) arranged external to the second flexible core 75. Each group of shape memory alloy wire elements 61-63, 71-73 includes shape memory alloy wire elements that are circumferentially spaced relative to one another. The first and third tubular elements 51, 53 each have one collet 81, 84 at an end thereof, and the second tubular element 52 includes two collets 82, 83 at ends thereof. The collets 81-84 include anchor points 85-88, respectively, for ends of the first and second groups of shape memory alloy wire elements 61-63, 71-73. The third tubular element 53 further includes a hollow body 80 including conductors 78 extending therethrough. In certain embodiments, each shape memory alloy wire elements 61-63, 71-73 is independently actuatable, such that three-dimensional pivotal movement may be provided between the first and second tubular elements 51, 52 across the first joint 60, and three-dimensional pivotal movement may be provided between the second and third tubular elements 52, 53 across the second joint 70. FIG. 3B is a side elevation view of the steerable surgical device 50 of FIG. 3A in a deflected state due to actuation of at least one shape memory alloy wire element 61 across the first joint 60, with such view being superimposed over a dashed line representation of the device 50 in a straight or undeflected state, showing a deflection angle δ therebetween.

FIG. 4 is a perspective view of a steerable surgical device 90 holding a MitraClip device 96, prior to percutaneous insertion. The steerable surgical device 90 includes first and second tubular elements 91, 92 with a joint 93 arranged therebetween 93, and a MitraClip device 96 extending beyond an end 98 of the steerable surgical device 90. Pivotal movement between first and second tubular elements 91, 92 may be effectuated by actuating shape memory alloy wire elements within the first and second tubular elements 91, 92, such as by conveying signals through conductors (not shown) internal to an upstream body portion 95 of the steerable surgical device 90.

FIG. 5A is a simplified schematic view of an apparatus 100 having two disc-shaped surfaces interconnected by three generally parallel shape memory alloy wire elements 103-105 in a pretensioned state, with the shape memory alloy wire elements 103-105 arranged approximately 120 degrees apart from one another.

FIGS. 5B and 5C illustrate pretensioning of shape memory alloy wire elements of a steerable surgical device that includes three shape memory alloy wire elements 131-133 positioned approximately 120 degrees apart from one another to enable control of pivotal movement between first and second tubular elements 111, 112. FIG. 5B includes first and second frames 5B-1, 5B-2, and FIG. 5C includes first and second frames 5C-1, 5C2. The first frames 5B-1, 5C-1 of FIGS. 5B and 5C respectively show first and second cross-sectional views (taken in opposing directions) of the two tubular elements 111, 112 with reduced diameter extensions 111', 112'. Frame 5B-1 of FIG. 5B shows a first anchor 121 within the interior cavity 115 of the first tubular element 111, and frame 5C-1 of FIG. 5C shows second and third anchors 122, 123 within the interior cavity 115 of the second tubular element 112. The second frames 5B-2, 5C2 of FIGS. 5B and 5C illustrate a flexible joint 113 (e.g., optionally embodying a sleeve or collar 114) arranged between the tubular elements 111, 112, and the positioning of shape memory alloy wire elements 131-133 within the first and second tubular elements 111, 112. In particular, the second frame 5B-2 of FIG. 5B shows a first shape memory alloy wire elements 131 terminating at a location within the first tubular element 111 (corresponding in placement to the first anchor 121 shown in the first frame 5B-1), while the second frame 5C-2 of FIG. 5C shows second and third shape memory alloy wire elements 132, 133 terminating at locations within the second tubular element 111 (corresponding in placement to the second and third anchors 122, 123 shown in the first frame 5C-1). The first shape memory alloy wire element 131 may be subjected to a first tensioning force $T_1$ as shown in FIG. 5B, while the second and third shape memory alloy wire elements may be subjected to second and third tensioning forces $T_2$ and $T_3$, respectively, as shown in FIG. 5C. In certain embodiments, the first through third tensioning forces $T_2$-$T_3$ may be substantially equal.

In certain embodiments, ends of shape memory alloy wire elements may be are arranged proximate to anchor points of a first tubular element, then wire sections fed through a joint into a second tubular element to cause intermediate points to contact anchor points of the second tubular element, and wire sections may be returned through the joint and into the first tubular element to cause ends to be proximate to anchor points of the first tubular element. Ends of the shape memory alloy wire elements may then pulled with a certain force (e.g., depending on the diameter of the shape memory alloy wire element) to place the memory alloy wire elements in tension. At that point, the first and second attachment points are then attached to anchor points of the first tubular element, to cause the shape memory alloy wire elements to be pretensioned.

Figure 6:
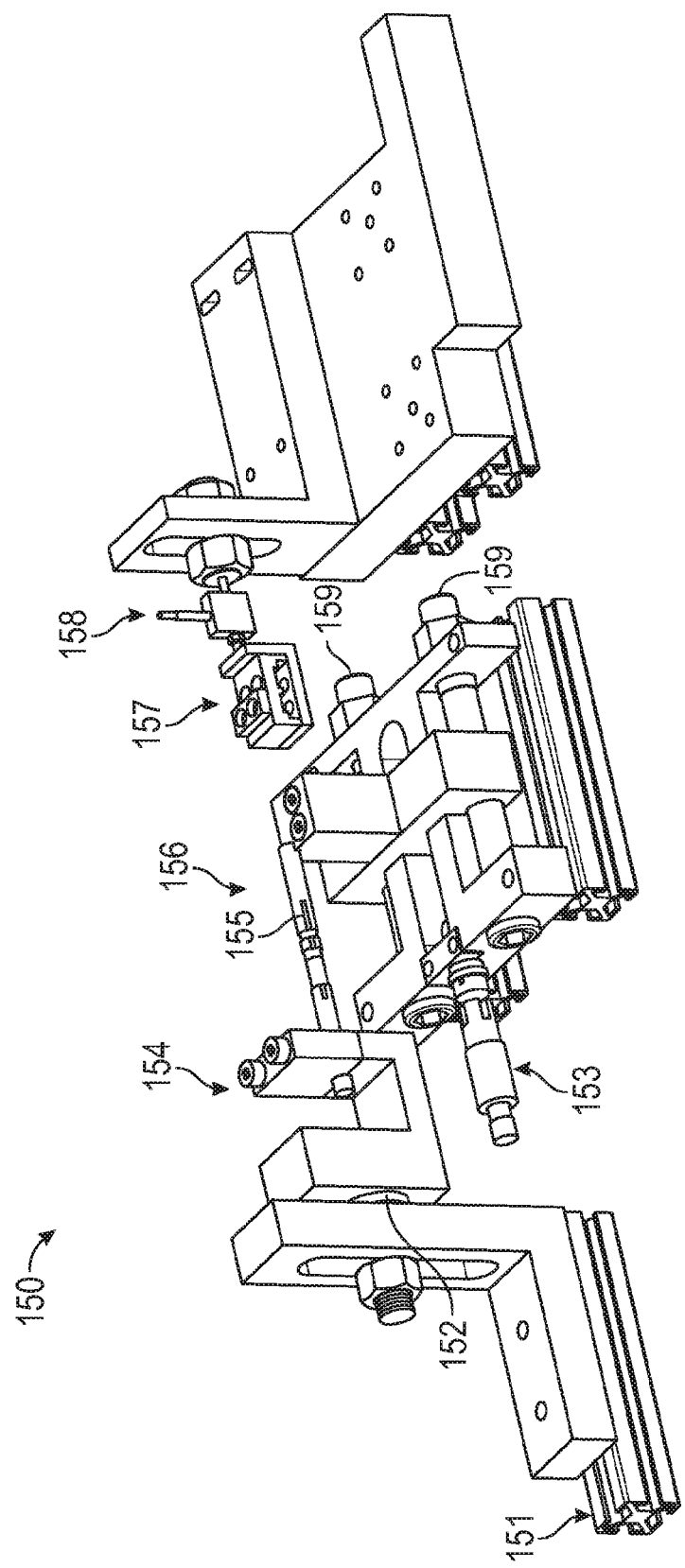
FIG. 6 is a perspective view of a system for pretensioning shape memory alloy wires of a steerable surgical device.

FIG. 6 is a perspective view of a system 150 for pretensioning shape memory alloy wires of a steerable surgical device. The pretensioning system 150 includes a main mounting frame 151, a bearing 152 for angular alignment, a micrometer 153, a holder jaw 154, shape memory alloy wire elements 155 associated with an a tubular active joint 156, wire holders 157, load cell 158, and adjusting pins 159 The holder jaw 154 is configured to hold the tubular active joint 156, and the bearing 152 is configured to permit rotation of the tubular active joint 156 to facilitate proper alignment. The wire holders 7 are configured to hold shape memory alloy wire elements, and the load cell 158 is configured to set the desired strain and stress on the shape memory alloy wire elements held by the wire holders 7. While movement of a left side of the tubular active joint 156 is restrained, the right side may be pushed to the left to create 150 MP of compressive stress on the tubular active joint 156 (e.g., optionally embodied in a Viton tube). At this point, the tubular active joint 156 may be glued to a second semi-tubular element (which may embody one or more three dimensionally printed parts). The shape memory alloy wire element 155 may be looped inside a channel on the left side of the tubular active joint 156. Then, the two free ends of the shape memory alloy wire element 155 may be attached to the 158 load cell and pulled (e.g., until a 150 MP of tension appears on wire). At this point, the shape memory alloy wire element 155 may be glued to a first semi-tubular element. This procedure may be repeated for all three shape memory alloy wire elements. When completed, semi-tubular subassembly portions may be glued together to form a final assembly.

FIGS. 7A-7C illustrate at least a portion of a steerable surgical device 160 according to another embodiment, wherein FIG. 7A provides an exploded perspective view, FIG. 7B provides a side elevation view, and FIG. 7C provides a cross-sectional view. Referring to FIGS. 7A-7C, the steerable surgical device 160 includes a first tubular element 162 (e.g., embodying a base shaft), a second tubular element 161 (e.g., embodied as a top shaft), and a joint 170 including a ball 172 configured to cooperate with a semispherical surface 166 of the first tubular element 161. The first tubular element 161 includes an outer end 163 and a wider, inner end 164 that opens to the semispherical surface 166. Three openings 165 are defined in the semispherical surface 166 and are registered with three anchors 167 (e.g., embodied in posts that protrude inwardly) in an interior of the first tubular element 161. The second tubular element 162 includes an inner end 174 that opens to a wide cavity 176 that leads to a tapped bore 178 proximate to an outer end 175. Three anchors 177 (e.g., embodied in posts that protrude inwardly toward a central axis of the wide cavity 160) are provided within the second tubular element 162. A central rod 171 includes a threaded portion 173 configured to be received by the tapped bore 178 of the second tubular element 162, and includes the ball 172 configured to be received by the semispherical surface 166 of the first tubular element 161. Three shape memory alloy wire elements (not shown) may be attached to the anchors 177 of the second tubular element 162, extend through the wide cavity 176 and through the holes 165 defined in the semispherical surface 166, and attached at to anchors 166 within the first tubular element 161.

Rotation of the central rod 171 relative to the second tubular element 162 can adjust spacing between the first and second tubular elements 161, 162 and tension applied to the shape memory alloy wire elements. Restated, adjusting the extent of threadable engagement between the central rod 171 and the tapped bore 178 of the second tubular element 162 serves to adjust the minimum distance between the first and second tubular elements 161, 162, thereby putting the shape memory alloy wire elements in tension.

FIGS. 8A and 8B illustrate a steerable surgical device 180, with a joint 183 including multiple joint segments 185-187 arranged between first and second tubular elements 181, 182. Each joint segment 185-187 includes a biasing spring 188 configured to maintain tension therein. FIG. 8C illustrates a joint-forming element 190 including a hollow interior 194, a base portion 191 defining a socket, and a bulbous portion 192 configured to be received by a socket of another joint-forming element. FIG. 8B is a magnified side elevation view of a central portion of the steerable surgical device 180 of FIG. 8A, with dashed line representation of internal structures including a socket 196 and shape memory alloy wire elements 189. Relative to single joint embodiments, a multi-segment joint 181 such as shown in FIGS. 8A and 8B may provide greater range of deflection and thereby enhance steering maneuverability.

Figure 9A:
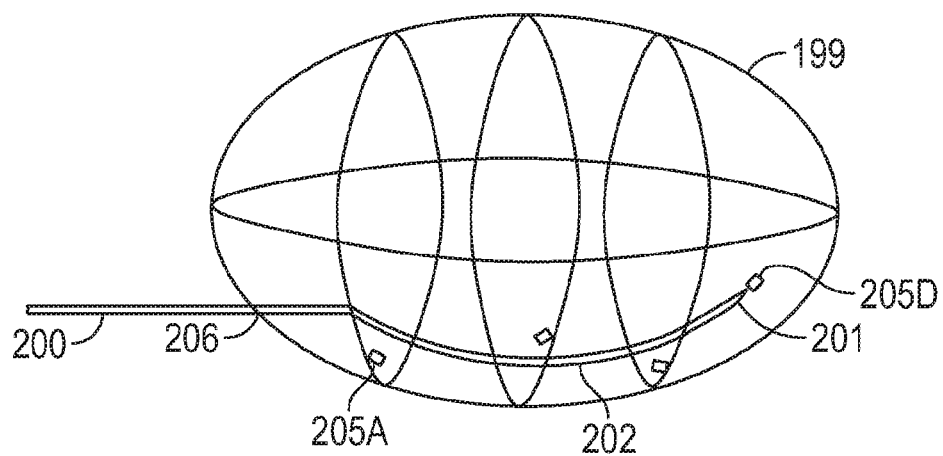
FIG. 9A is a schematic view illustration of a conventional flexible needle being manipulated within an organ proximate to multiple specific targets following introduction into the organ through a single insertion point.
Figure 9B:
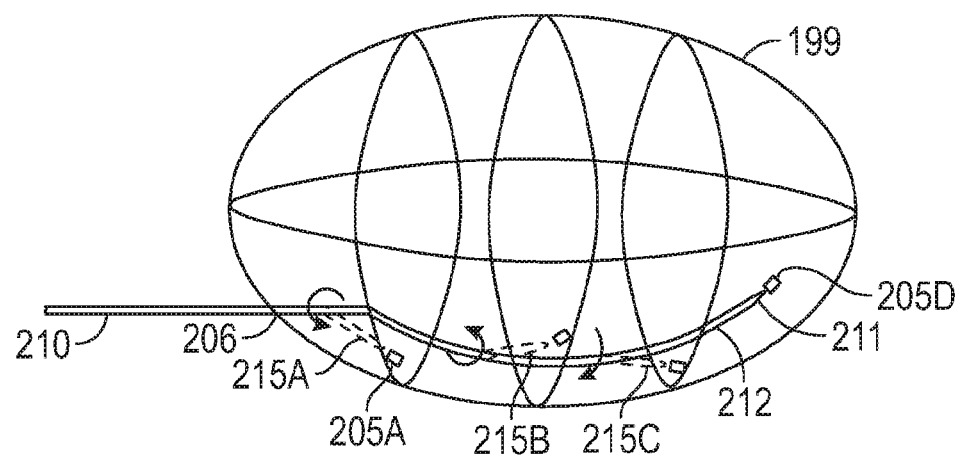
FIG. 9B is a schematic view illustration of a steerable surgical device according to one embodiment of the present disclosure being manipulated within an organ to directly access multiple specific targets (with intermediate trajectories shown in dashed lines) following introduction into the organ through a single insertion point.

FIGS. 9A and 9B permit comparison of a conventional flexible needle and a steerable surgical needle-type device following insertion into an organ through a single insertion point. FIG. 9A is a schematic view illustration of a conventional flexible needle 200 (having a flexible end portion 202 in a curved configuration proximate to a needle tip 201) being manipulated within an organ 199 proximate to multiple specific targets 205A to 205D following introduction of the needle 200 into the organ 199 through a single insertion point 206. The flexible needle 200 gets near, but does not directly access, several of the specific targets 205A to 205D within the organ 199.

FIG. 9B is a schematic view illustration of a steerable surgical needle-type device 210 (having a steerable end portion 212 shown in a curved configuration proximate to a needle tip 211) according to an embodiment of the present disclosure being manipulated within an organ 199 to directly access multiple specific targets 205A-205D following introduction of the device 210 into the organ 210 through a single insertion point 206. Intermediate trajectories 215A to 215C of the needle tip 211 are shown in dashed lines. As shown in FIG. 9B, use of a steerable surgical needle-type device 210 and multiple intermediate trajectories permits the device 210 to directly access each of the specific targets 205A to 205D. Such capability is facilitated by the reliability, predictability, and precision of the shape memory alloy elements.

Figure 10A:
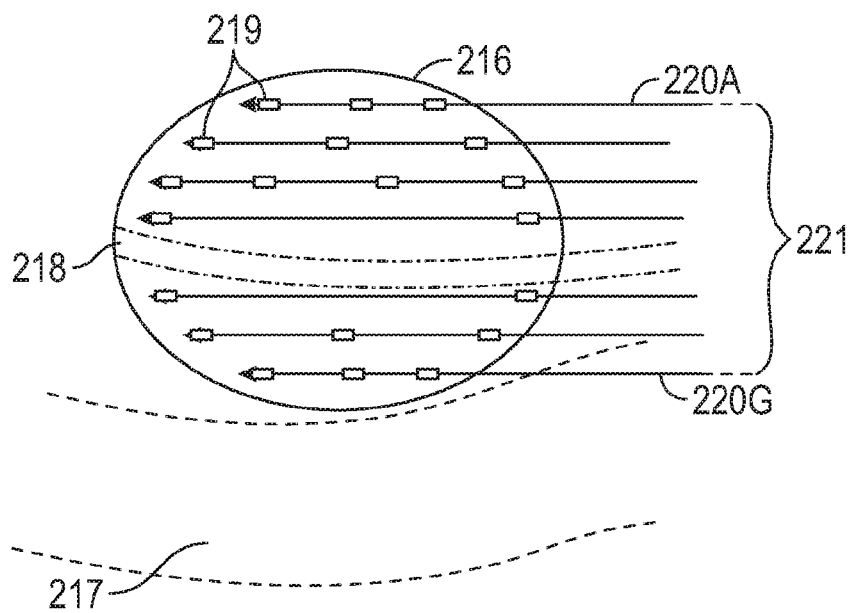
FIG. 10A is a schematic view illustration of paths taken by a conventional straight needle during a process of delivering radioactive seeds to multiple target sites within a prostate gland through seven insertion points.
Figure 10B:
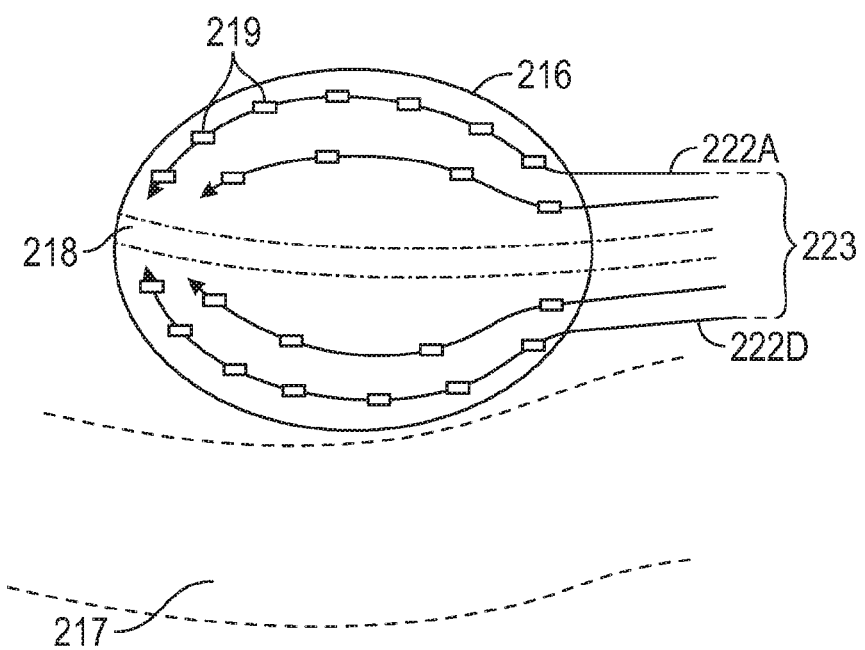
FIG. 10B is a schematic view illustration of paths taken by a steerable surgical device according to one embodiment of the present disclosure during a process of delivering radioactive seeds to a similar number of target sites within a prostate gland through four insertion points.

FIGS. 10A and 10B permit comparison of operation of a conventional straight needle and a steerable surgical needle-type device through multiple insertion points in a surgical process. FIG. 10A is a schematic view illustration of needle paths 220A to 220G taken by a conventional straight needle during a process of delivering radioactive seeds through several insertion points to multiple target sites 219 within a prostate gland 216, which surrounds a urethra 218 is positioned proximate to a rectal wall 217. Needle paths 220A to 220G (shown as seven in number) are selected to avoid puncture of the urethra 218 but still distribute radioactive seeds to widely distributed target sites 219. To provide the desired distribution of radioactive seeds using a conventional straight needle, a large aggregate puncture area 221 is required.

FIG. 10B is a schematic view illustration of paths 222A to 222D taken by a steerable surgical device according to one embodiment of the present disclosure during a process of delivering radioactive seeds to a similar number of target sites 219 within a prostate gland 216 (also surrounding a urethra 218 and positioned proximate to a rectal wall 217), but through a smaller number of insertion points (e.g., four in number) encompassing a smaller aggregate puncture area 223 relative to the puncture area 221 of FIG. 10A. The number of insertion points (e.g., puncture areas) is decreased because the steerable surgical device is able to access a wider range of areas from each puncture. The ability to deliver a similar distribution of radioactive seeds to a prostate gland 216 through a smaller aggregate puncture area 223 while avoiding sensitive structures (e.g., urethra 218 and rectal wall 217) may provide beneficial effects such as reduced risk of infection and improved healing time.

Figure 11:
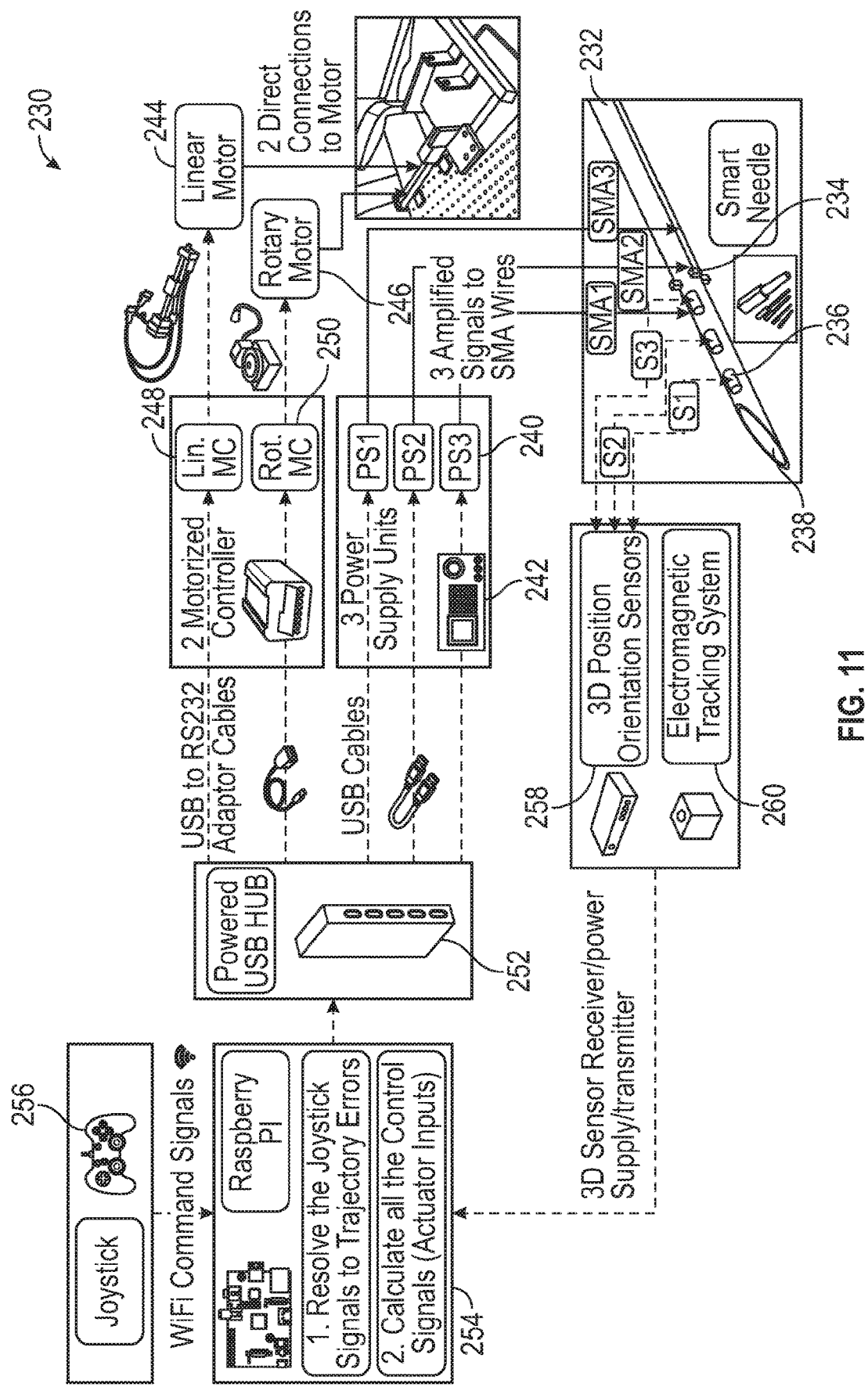
FIG. 11 is a diagram illustrating interconnections between various components of a steerable surgical device operating system according to one embodiment of the present disclosure.

FIG. 11 is a diagram illustrating various components of a steerable surgical device operating system 230 according to one embodiment of the present disclosure. Such system 230 includes a steerable surgical device 232 including multiple (e.g., three) shape memory alloy elements 234 (which may also be referred to as actuators; labelled as SMA1 to SMA3) and one or more sensors 236 (e.g., for feedback control of the actuators; labelled as S1 to S3), with the shape memory alloy elements 234 and sensors 236 arranged generally proximate to a tip 238 of the steerable surgical device 232. The three shape memory alloy elements 234, which are independently actuatable, are separately coupled with three power supply units 240 (labelled PS1 to PS3) of a power supply component 242. Actuation of the first to third shape memory alloy wire elements 234 controls deflection of the tip 238 of the steerable surgical device 232. The steerable surgical device 232 is coupled with a linear motor 244 (to control insertion distance) and a rotary motor 246 (to control rotation), with the foregoing motors 244, 246 being coupled to corresponding motor controllers 248, 250. The motor controllers 248, 250 and the power supplies 240 may be arranged downstream of a USB hub 252 (or other multi-signal interface component), which is coupled to a controller 254. An operator input device 256 (e.g., joystick, optionally wireless in character) may be further coupled to the controller 254, which may be embodied in a personal computer, a special purpose-computer, a programmable logic controller, an application specific integrated circuit, or the like. The controller 254 is also coupled with three dimensional position orientation sensing elements 258 (themselves being coupled with the sensors 236 of the steerable surgical device 232) and an electromagnetic tracking system 260 to enable detection of position of the steerable surgical device 232 within a patient. Operation of the steerable surgical device may be manually controlled (e.g., by a surgeon using the operator input device 256) and/or automatically controlled (e.g., by the controller 254 according to a pre-defined or operator-defined routine or sequence of steps). In certain embodiments, the steerable surgical device operating system 230 may be completely automated, thereby allowing the delivery of drugs to target areas and/or other therapeutic procedures to be performed with high precision.

It has been previously described herein that actuation behavior of shape memory alloys is generated when an internal crystalline transformation happens with application of load or heat. The transformation between Austenite (high temperature) and Martensite (low temperature) states is not thermomechanically reversible, and thereby creates a temperature hysteresis. Motion control of shape memory alloys is complicated due to hysteresis, nonlinear response characteristics, and measurement uncertainty with shape memory alloy characteristic parameters.

The nonlinear response of shape memory alloys and their material properties, such as transformation stress and temperature, are history and path-dependent. As a result, predicting the response of devices incorporating shape memory alloys may be challenging. To obtain a more consistent response of shape memory alloys under thermomechanical loadings, material training is desirable. Training results in permanent stress that will lead to formation of a preferred Martensitic variant in the absence of external load. The secondary effects of the training are changes in transformation temperatures, change in hysteresis magnitude, and a decrease in the macroscopic transformation strain.

Experimental and finite element analyses were performed to demonstrate the feasibility of 3D manipulation of an active needle via three SMA wires. A one-dimensional constitutive material model of shape memory alloys (developed by L. C. Brinson, J. Intell. Mater. Syst. Struct. pp. 229-242, 1993) was used. The interactions between the SMA wires arranged evenly around the needle body and their interactions were studied, and controllable deflection of an active needle was predicted. Performance of an active needle actuated by a single SMA wire was evaluated.

Figure 12:
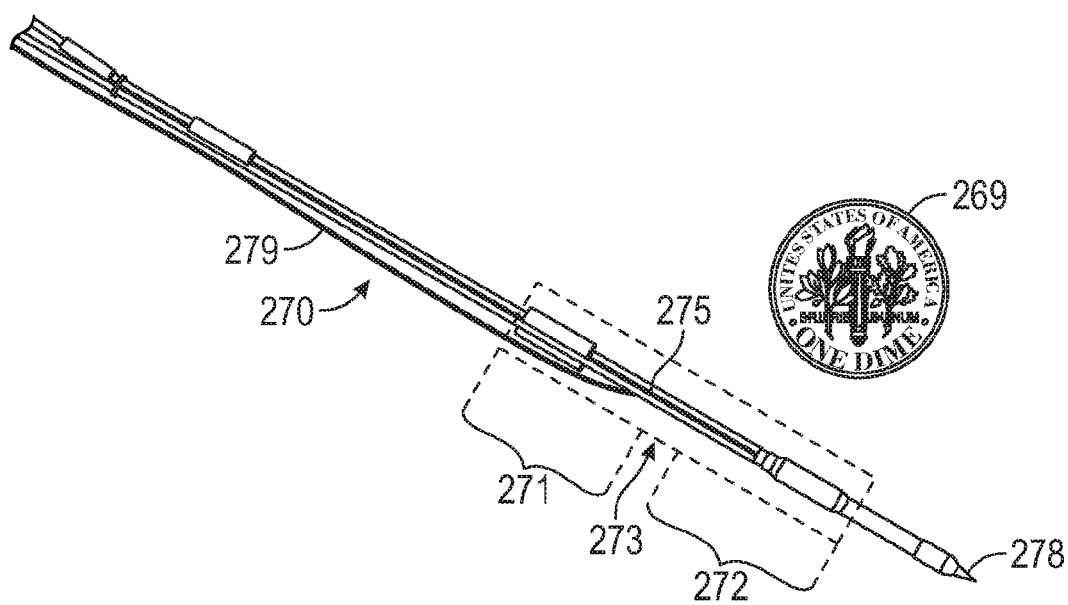
FIG. 12 illustrates a prototype of an active needle with a single shape memory alloy actuator, arranged next to a dime coin (U.S. ten cent coin) for scale.

FIG. 12 illustrates a prototype of an active needle 270 with a single shape memory alloy wire actuator 275, arranged next to a dime coin 269 (i.e., U.S. ten cent coin) for scale. First and second Nitinol tubes 271, 272 of 2.0 mm outer diameter and 1.2 mm inner diameter were used for the needle body. A flexible Nylon component 273 was arranged between the Nitinol tubes 272, 272 to provide a higher flexibility region. A shape memory alloy wire 275 of 0.2 mm diameter was used as an actuator. Small insulating crimps were used to secure the shape memory alloy wire 275 to the Nitinol tubes 271, 272. A lead copper wire 279 was inserted inside the crimp with a proper electrical conduction tape to actuate the shape memory alloy wire 275 via joule heating. The prototype active needle 270 showed a considerable deflection of 16.76 mm at the needle tip 278 via actuation of an 80 mm long shape memory alloy wire 275.

A model with a single shape memory alloy wire was developed in ANSYS (CAE Systems, Canonsburg, Pa., USA) including a total of 1436 finite elements, with the dimensions of the prototype described above, wherein only the part of the active needle affected by actuators was modeled. Three dimensional hexagonal elements (according to SOLID186, a higher order three dimensional 20-node solid element that exhibits quadratic displacement behavior) were used to discretize the model and create a mesh. Mesh refinement was applied to the areas that the shape memory alloy wire was connected to the needle body. The mesh was also refined in the areas that the needle tubes were connected to the flexible Nylon component.

Figure 13:
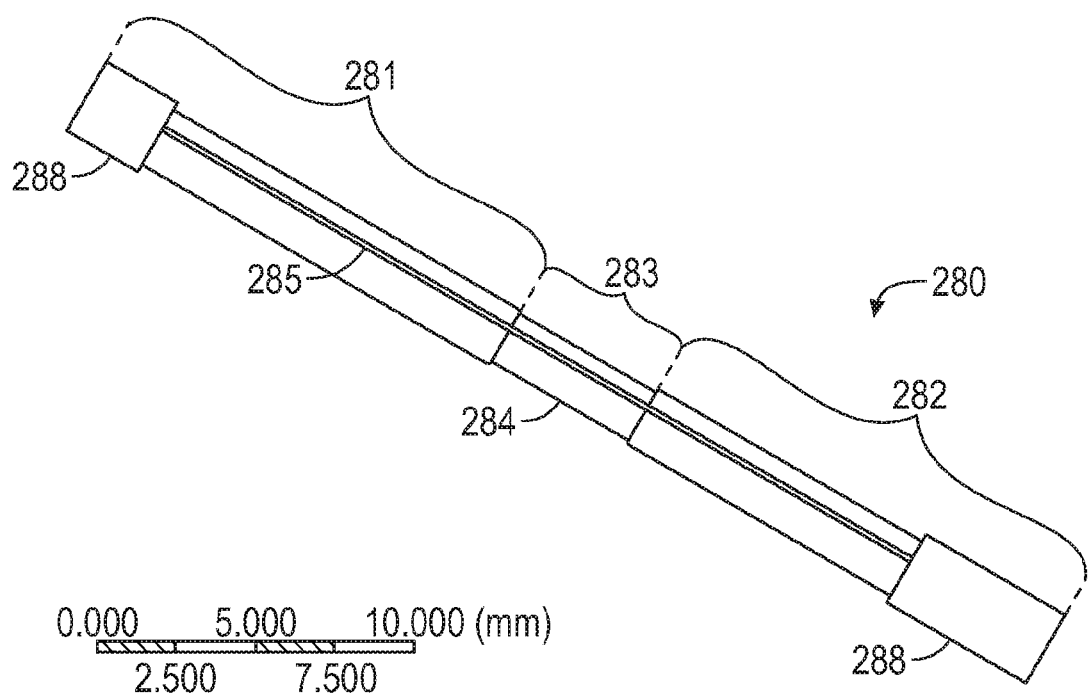
FIG. 13 is an outline of a finite element representation of an actuatable portion of an active needle having an external shape memory alloy wire actuator, in an undeflected state.
Figure 14:
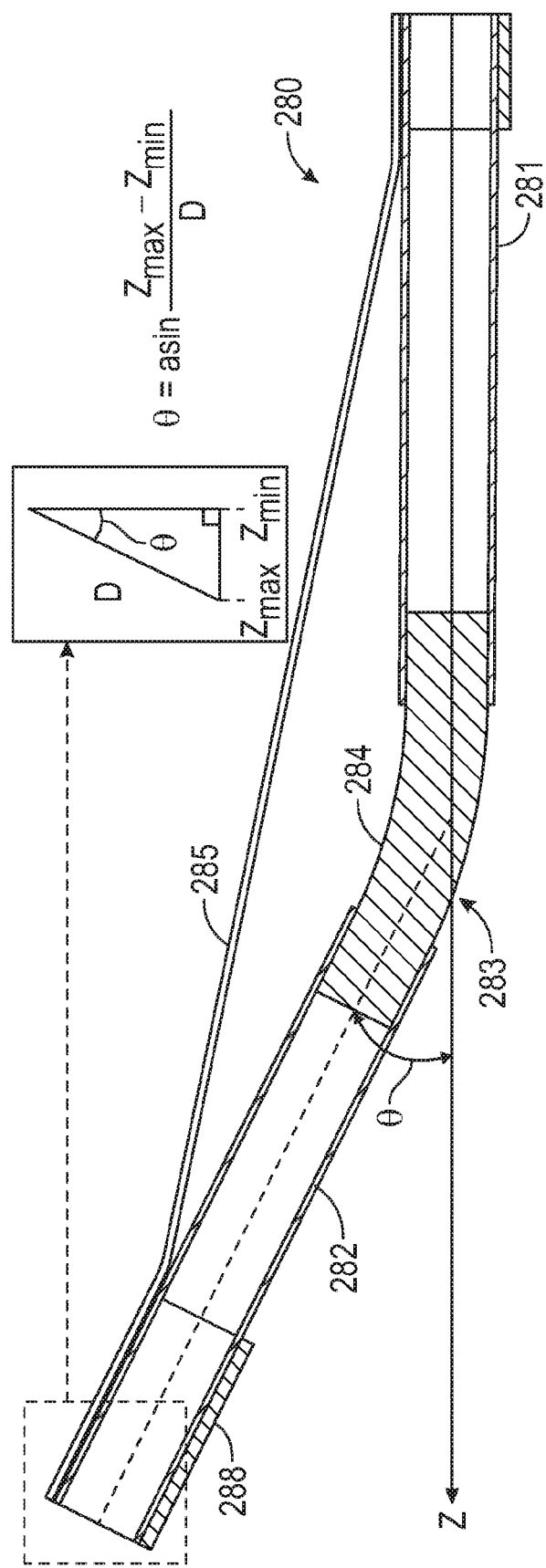
FIG. 14 is an outline of a finite element representation of an active needle with an external shape memory alloy wire actuator, in a deflected state, with a superimposed trigonometric relation to calculate angular deflection of the active needle.

FIG. 13 is an outline of a finite element representation of an actuatable portion of active needle 280 having an external shape memory alloy wire actuator 285, in an undeflected state. The modeled active needle 280 includes a Nylon component 284 serving as a joint 283 between first and second tubular elements 281, 282 of Nitinol material, with a single external shape memory alloy wire actuator 285 being retained at ends thereof by crimps 288. The material properties of the Nitinol tubes and the Nylon component were selected from the material library of ANSYS; however, to model the actuation behavior of shape memory alloys a thermal expansion coefficient was included to imitate their contraction response. To compare the experimental evaluation with finite element modeling results, the angular deflection of the needle at the joint was compared. Since angular deflection of a body cannot be directly determined by ANSYS, a trigonometric relation was developed based on the z-directional displacement of the nodes shown in FIG. 14 calculate the overall angular deflection of the needle. FIG. 14 is an outline of a finite element representation of the active needle of FIG. 13 in a deflected state, with a superimposed trigonometric relation to calculate angular deflection of the active needle. The second tubular element 282 is shown as pivoted upward at the joint 283 relative to the first tubular element 281 by an angle θ.

Figure 15:
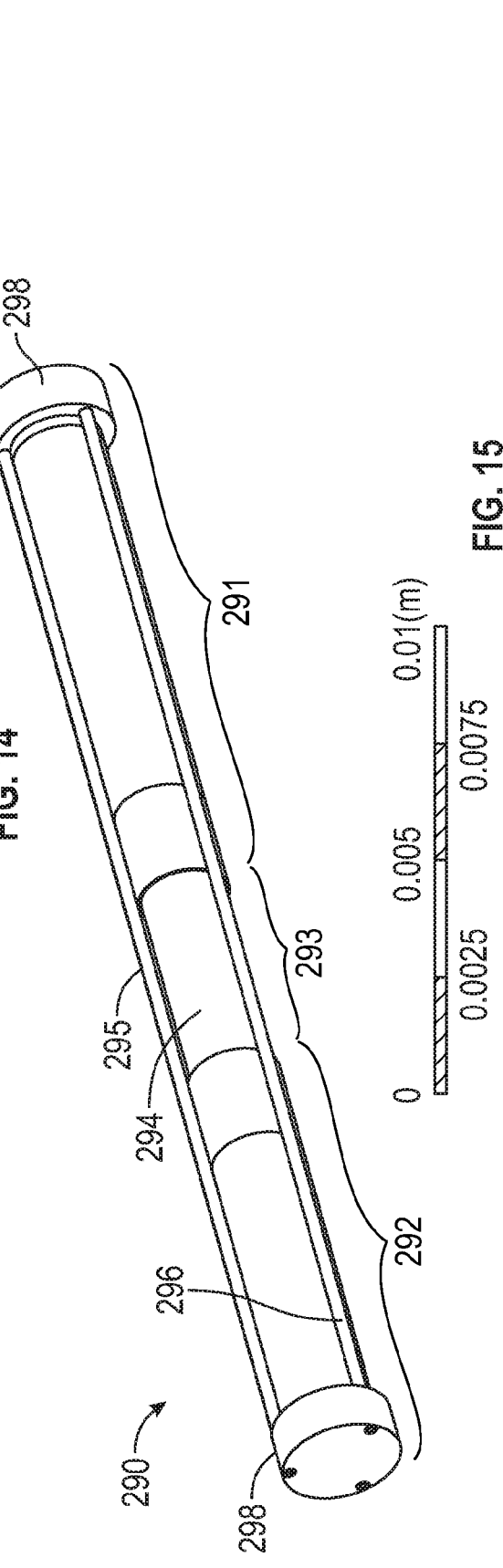
FIG. 15 is an outline of a finite element representation of another active needle with three external shape memory alloy wire actuators, in an undeflected state.

To enable three-dimensional manipulation, an active needle having three circumferentially spaced shape memory alloy actuators was modeled. FIG. 15 is an outline of a finite element representation of such an active needle 290 having three external shape memory alloy wire actuators 295, 296 (another not shown), in an undeflected state. The modeled active needle 290 includes a Nylon component 294 serving as a joint 293 between first and second tubular elements 291, 292 of structural steel (having 2.6 mm outer diameter and 1.8 mm inner diameter), with three external shape memory alloy wire actuators 295, 296 (another not shown) of Flexinol® (Dynalloy, Inc., Irvine, Calif.) nickel-titanium shape memory alloy wire having 0.2 mm diameter retained at ends thereof by crimps 298. The foregoing elements were meshed with 3D hexagonal elements.

Figure 16A:
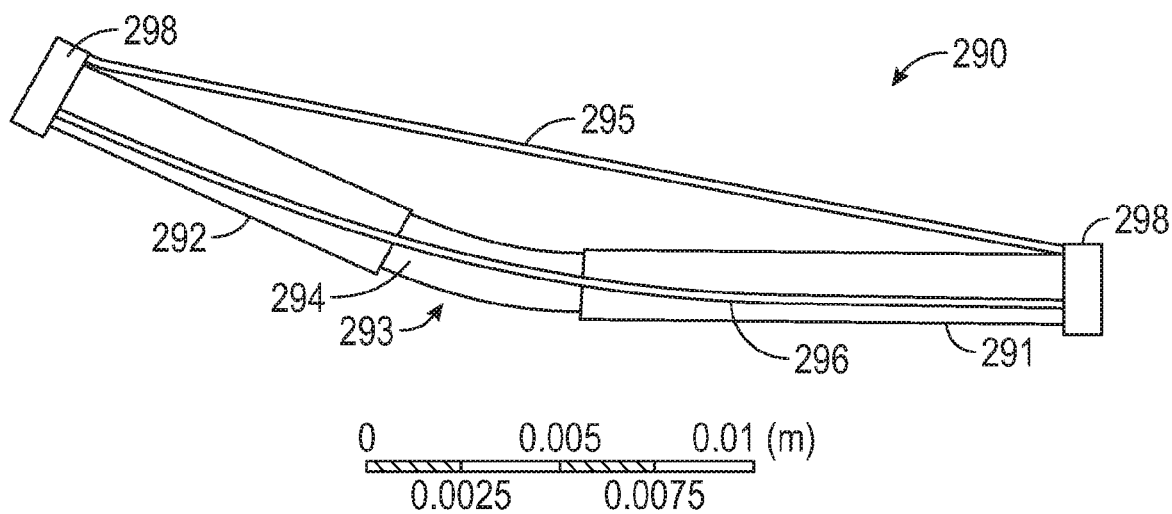
FIG. 16A is an outline of a finite element representation of the active needle of FIG. 15 in a deflected state with a first shape memory alloy wire actuator being actuated to its maximum contraction.
Figure 16B:
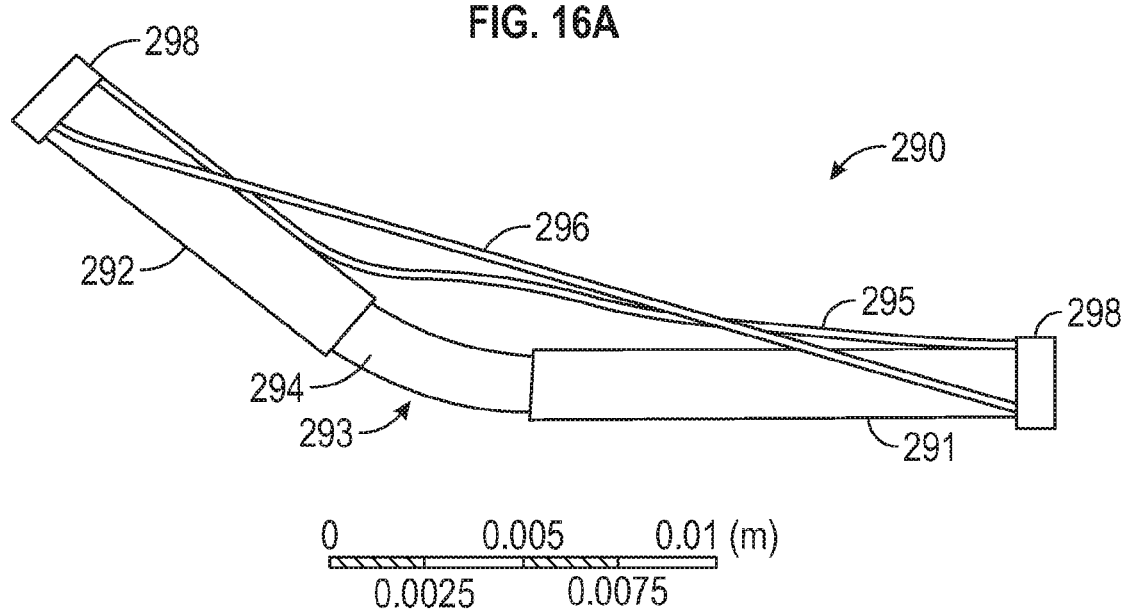
FIG. 16B is an outline of a finite element representation of the active needle of FIG. 15 in a deflected state with the first shape memory alloy wire actuator remaining heated while the second and third shape memory alloy wire actuators are actuated.

FIGS. 16A and 16B provide results of initial studies of deflection associated with the contraction of shape memory alloy wire actuators. FIG. 16A is an outline of a finite element representation of the active needle 290 of FIG. 15 in a deflected state with a first shape memory alloy wire actuator 295 being actuated to its maximum contraction (5% strain). Then while the first shape memory alloy wire actuator 295 remained heated, the second and third shape memory alloy wire actuators (e.g., 296) were actuated to see if the wires could recover the initial shape of the active needle 290. FIG. 16B is an outline of a finite element representation of the active needle of FIG. 15 in a deflected state with the first shape memory alloy wire actuator remaining heated while the second and third shape memory alloy wire actuators are actuated. It can be observed in FIG. 16B that instead of pulling the needle tip downward as intended, the second and third shape memory alloy wire actuators caused even more deflection, while the first shape memory alloy wire actuator buckled and was in a loosened shaped. To fix this issue, a set of assumptions and loading conditions were adopted to generate a desired operation.

Figure 17:
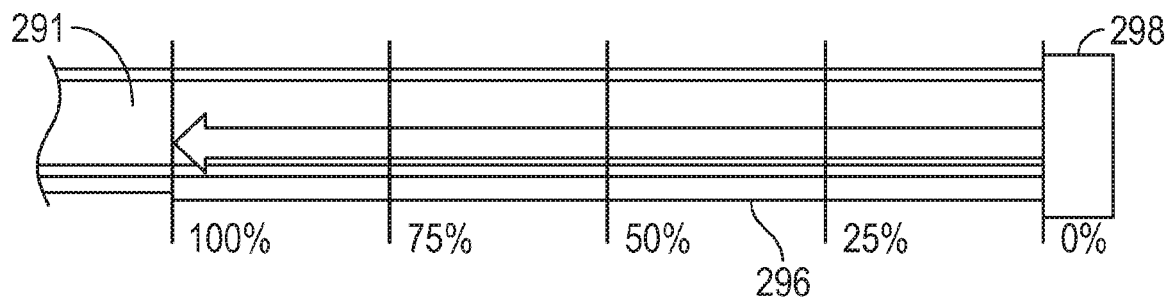
FIG. 17 is a schematic diagram showing the bonded length of a shape memory alloy wire element attached to a needle tube, with a superimposed length scale including twenty-five percent increments.
Figure 18:
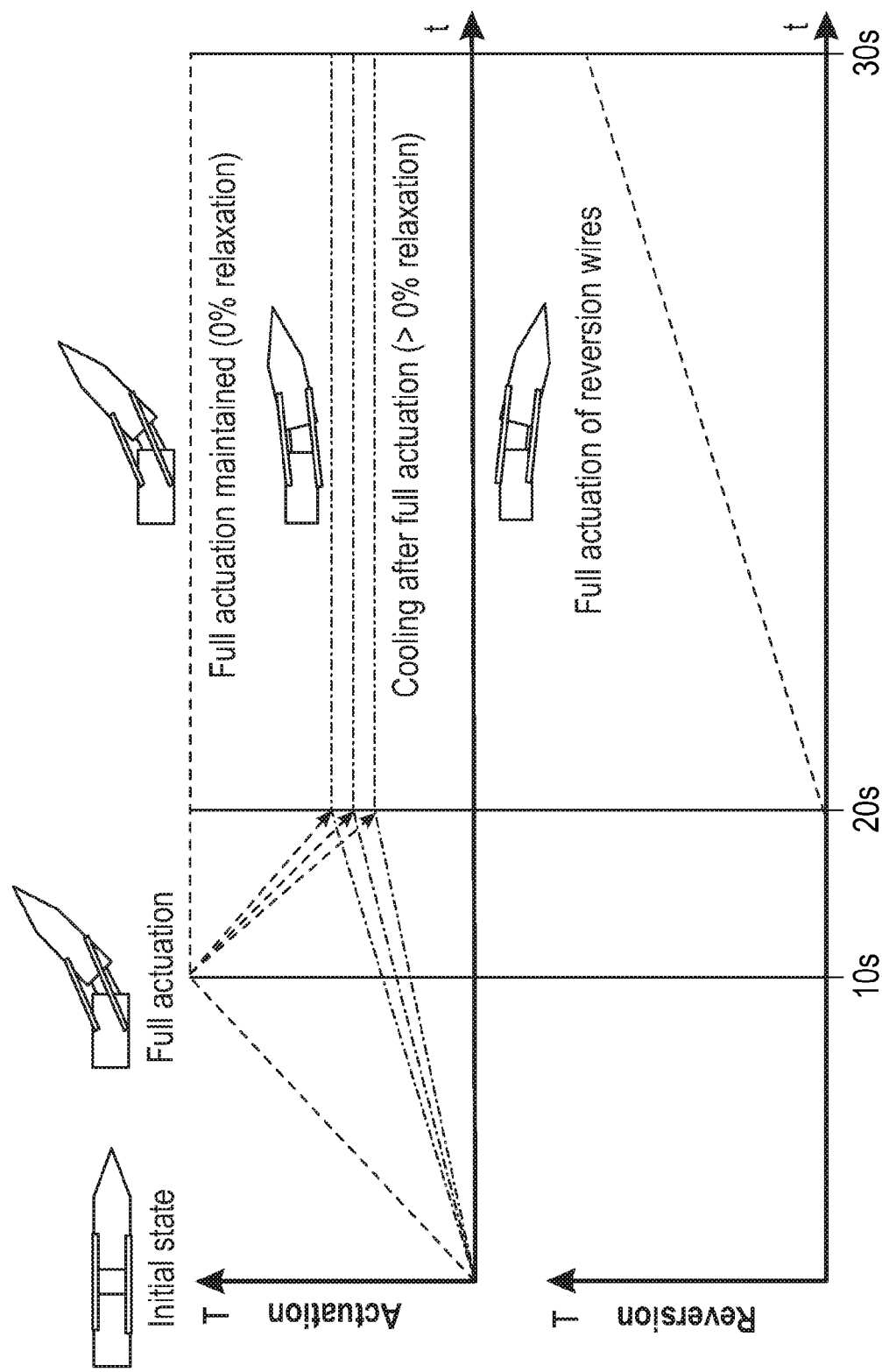
FIG. 18 provides plots of temperature versus time for actuation (upper frame) of the first shape memory alloy wire element of FIG. 16A, and reversion (lower frame) of the first shape memory alloy wire element of FIG. 16A during partial cooling before actuation of the opposing second and third shape memory alloy wire elements.

Case studies were performed to investigate the reversion of the active needle via assistance of the shape memory alloy wire actuators on opposite sides. It was considered that a first shape memory alloy wire actuator would relax (cool down) after its full actuation, and then recover to its 25 and 50% of maximum contraction prior to actuation of the other two shape memory alloy wire actuators. A relaxation factor (R=0, 25%, and 50%) was defined to study the response of the active needle under these conditions. FIG. 17 is a schematic diagram showing the bonded length of a shape memory alloy wire element attached to a needle tube, with a superimposed length scale including twenty-five percent increments. Results of the case studies to investigate reversion of the active needle via assistance of shape memory alloy wire actuators on opposite sides are provided in FIG. 18. FIG. 18 provides plots of temperature versus time for actuation (upper frame) of the first shape memory alloy wire element of FIG. 16A, and reversion (lower frame) of the first shape memory alloy wire element of FIG. 16A during partial cooling before actuation of the opposing second and third shape memory alloy wire elements. As shown in FIG. 18, shape memory alloy actuator activation steps include actuation of the first shape memory alloy actuator, and partial cooling of the first shape memory alloy actuator before actuation of the opposing shape memory alloy actuators.

Figure 19:
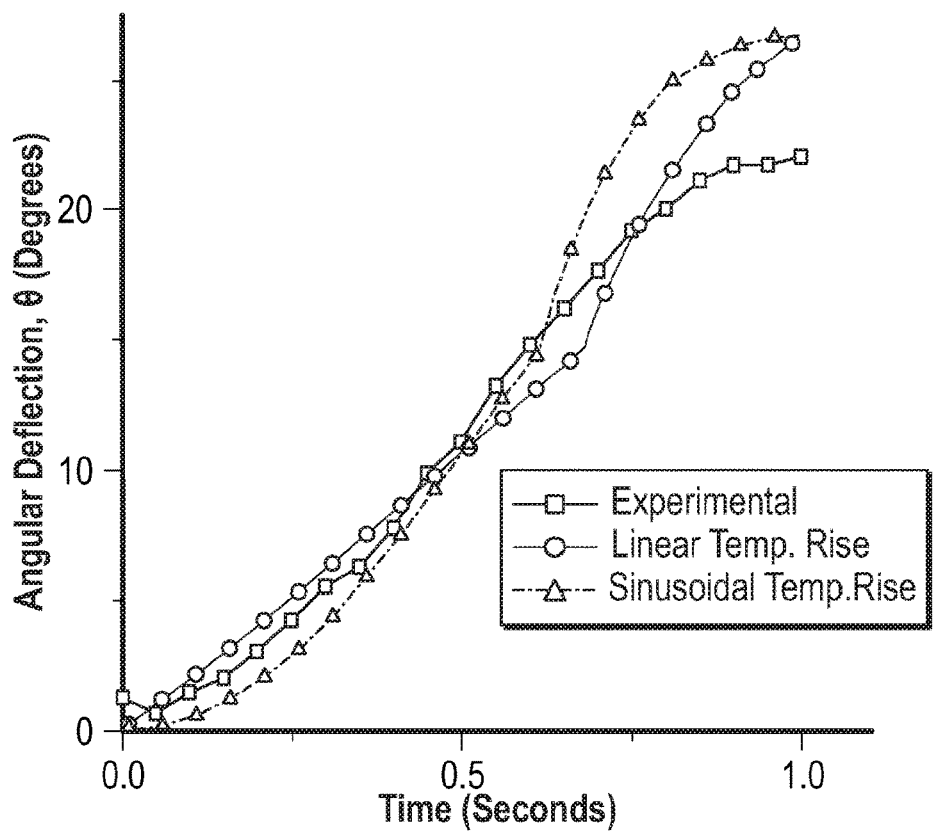
FIG. 19 provides superimposed plots of angular deflection versus time for experimentally observed active needle deflection and for prediction by finite element analysis.

FIG. 19 provides superimposed plots of angular deflection versus time for experimentally observed active needle deflection (for the prototype needle including a single actuator) and for prediction by finite element analysis. A good agreement for the angular deflection was found, and therefore confirming the finite element approach. Temperature of the shape memory alloy wire was raised using a linear (ramp) and a sinusoidal function. The finite element modeling also demonstrated that both simple linear and sinusoidal temperature loading condition could be used to contract the shape memory alloy wires. The results showed that even with the thermal expansion model of shape memory alloys, the transient response of the needle could be predicted by the finite element model.

Figure 20:
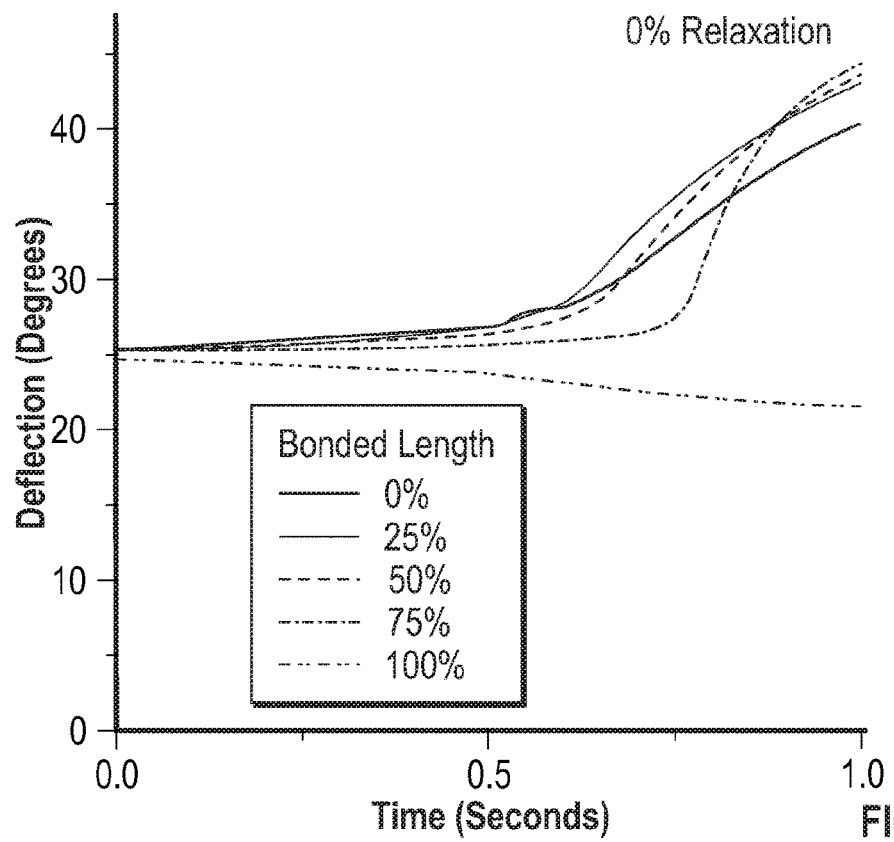
FIG. 20-22 provide plot of angular deflection versus time obtained by an active needle reversion case study with 0%, 25%, and 50% relaxation, respectively, of the first shape memory alloy wire element of FIGS. 15 and 16A.
Figure 21:
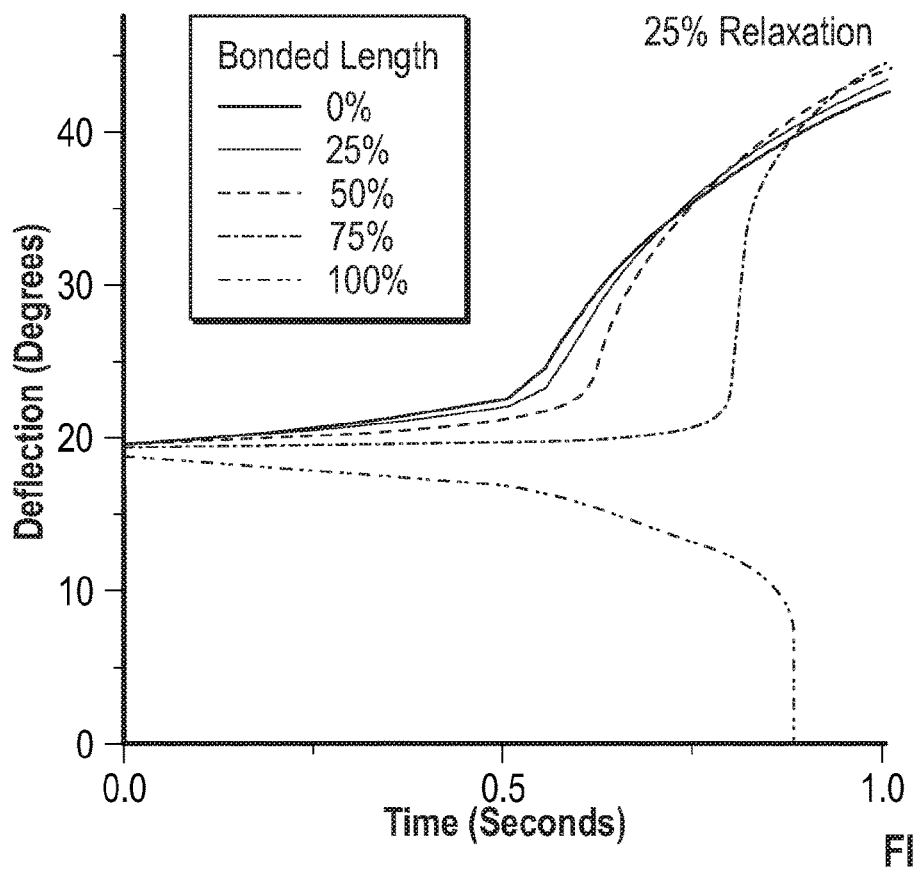
Figure 22:
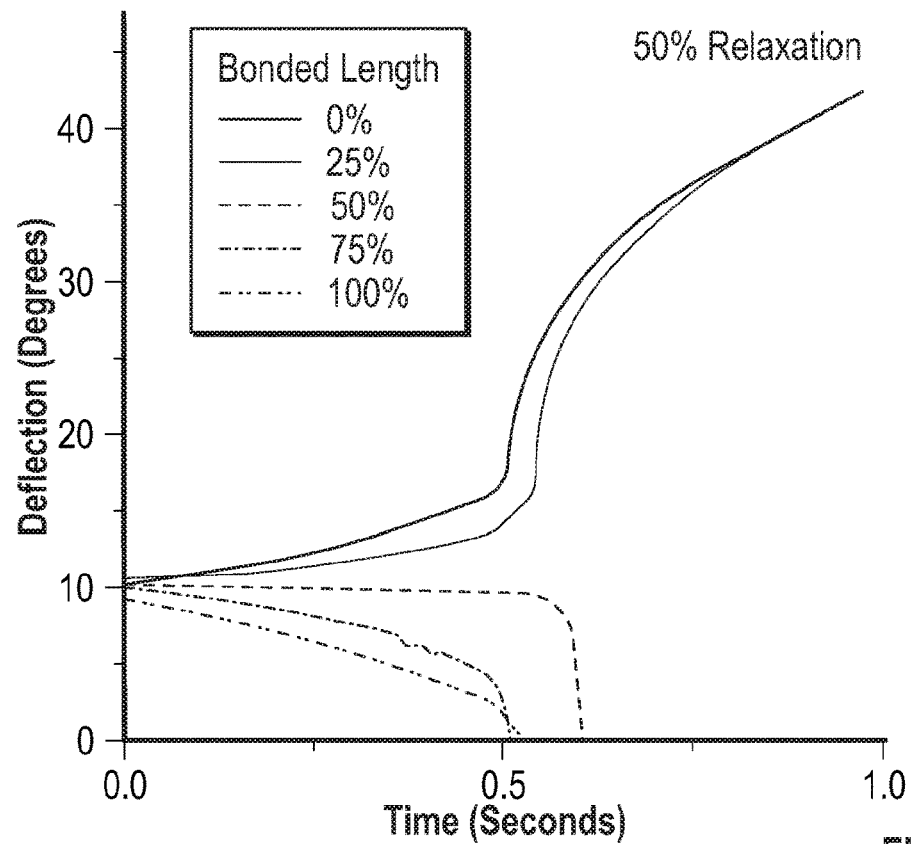

FIGS. 20-22 provide results for active needle reversion case studies for an active needle with three shape memory alloy actuators (according to FIG. 15) with different levels of relaxation for the first shape memory alloy actuator, namely: no relaxation (FIG. 20), 25% relaxation (FIGS. 21), and 50% relaxation (FIG. 22.)

FIG. 20 presents the case in which the firs shape memory alloy actuator is kept actuated to its maximum contraction (with no relaxation), while the second and third shape memory alloy actuator are intended to recover the needle to its initial shape via their actuation forces. An angular deflection of 26 degrees was found at maximum contraction of the first shape memory alloy actuator. It was seen that recovery of the needle could not be obtained. In most cases, the opposing second and third shape memory alloy actuators worked in favor of the initial actuation, and thereby caused more deflection. It was only through 100% bonded length of the second and third shape memory alloy actuators that needle recovery was possible. A rapid deflection was observed at bonded length (BL)=75% when the second and third shape memory alloy actuators were actuated; this could result in a sudden movement and a probable tissue rupture FIG. 21 shows the case where the first shape memory actuator is cooled down and recovered to its 25% of maximum contraction prior to the actuation of the second and third shape memory actuators. The overall angular deflection was decreased to 19 degrees since the first shape memory actuator was partially relaxed. The same trend seen in FIG. 20 is exhibited in FIG. 21. Only with 100% of bonded length could the second and third shape memory actuators cause deflection of the active needle back to its shape when fully actuated. Similarly, a rapid deflection was observed with 75% of bonded length.

FIG. 22 shows the case where the first shape memory alloy actuator is 50% relaxed before actuation of the opposing second and third shape memory alloy actuators. An angular deflection of 11 degrees was seen since the first shape memory alloy actuator was relaxed to its half of maximum contraction. It was seen that with a bonded length of 50-100%, the second and third shape memory alloy actuators would cause deflection in the opposite direction. A rapid deflection was seen at a bonded length of 50% in this case.

Figure 23:
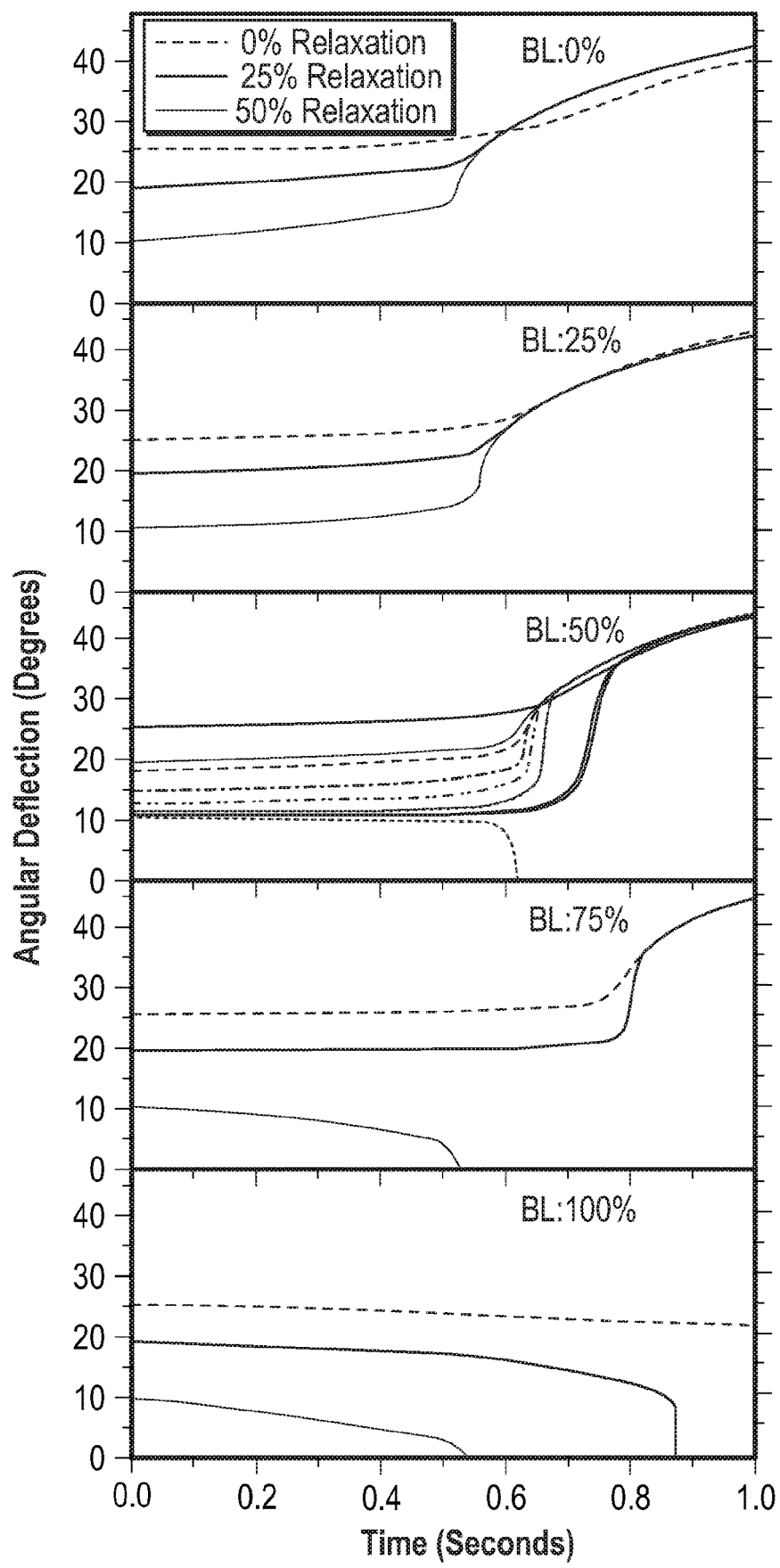
FIG. 23 provides plots of angular deflection versus time of an active needle incorporating multiple shape memory alloy wire elements, with the bonded length of the actuator being varied from 0% percent in an uppermost frame to 100% in a lowermost frame, and intermediate frames with bonded length being varied in 25% increments.

FIG. 23 provides plots of angular deflection versus time of an active needle incorporating multiple shape memory alloy wire elements, with variation in bonded length (i.e., bonded length (BL) of the shape memory alloy actuator being varied from 0% percent in an uppermost frame to 100% in a lowermost frame, and intermediate frames with bonded length being varied in 25% increments). It can be seen that with BL=0 or 25%, no recovery could be achieved. However, with 50 and 70% of bonded length, only the cases where the initial actuation is relaxed to its 50% can be recovered. If the actuators are 100% bonded to the needle, though, then no relaxation is required to recover the initial shape of the needle. Through the combinations of the bonded length and relaxation parameters, namely $0\% \leq BL \leq 100\%$ and $0\% \leq R \leq 50\%$, it was found that active needle shape recovery is possible at certain configurations. The data showed that the best reversion would happen in cases where the actuators are pinned along the needle body. It was also seen that to recover a partial deflection, a bonded length and a relaxation factor of up to 50% could also play an assistive role for needle's reversion. Another important feature to note is that a rapid deflection can occur as the bonded length approaches some critical values at relaxations of 25 and 50%. This may imply that the active needle can cause sudden rupture in the tissue if both actuation and reversion are not properly controlled.

Figure 24:
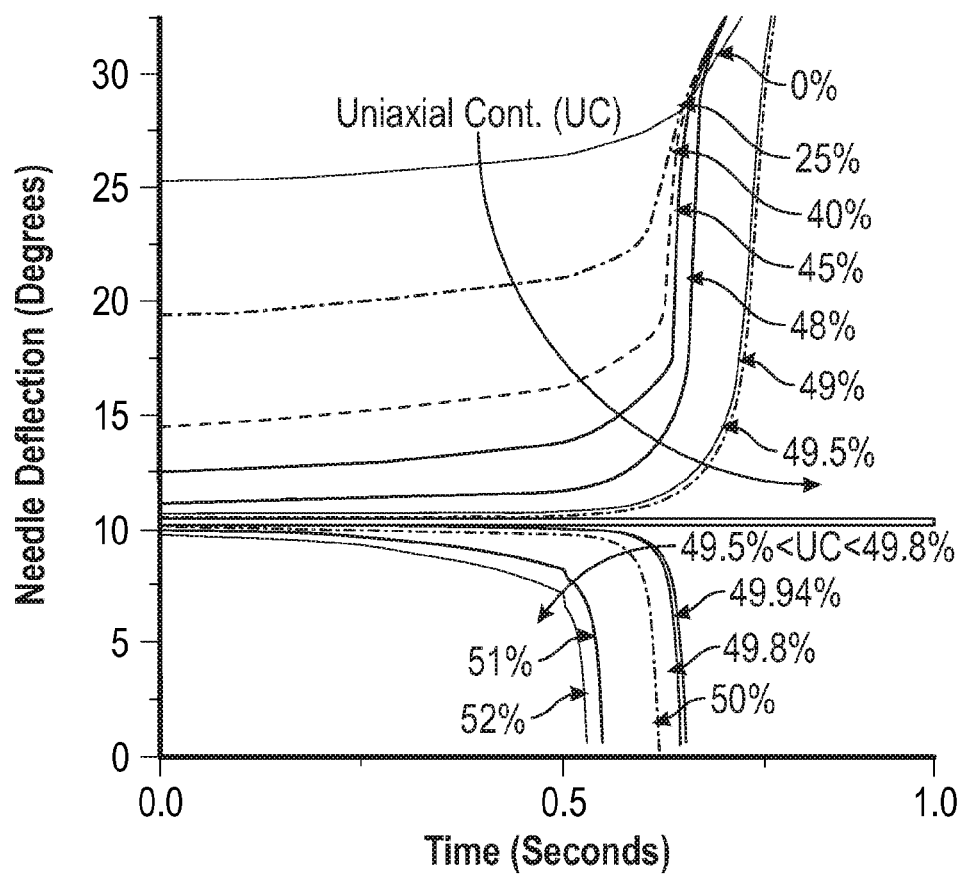
FIG. 24 is a plot of angular deflection versus time of an active needle having 50% bonded length, for different relaxation values.

It was seen from previous data that with 50% of bonded length, there is a high chance of recovering the needle's initial shape. However, the initial actuator must relax to some level before the recovery could be realized. Therefore, data was collected (shown in FIG. 24) in a case where bonded length was kept at 50%, while the relaxation was changed between zero to 52% with higher resolution in the more sensitive areas. FIG. 24 is a plot of angular deflection versus time of an active needle having 50% bonded length, for different relaxation values. It was seen that around 50% of relaxation, control of the needle is difficult since both recovery and additional deflection could happen with slight changes in initial relaxation of a shape memory alloy wire.

Figure 25:
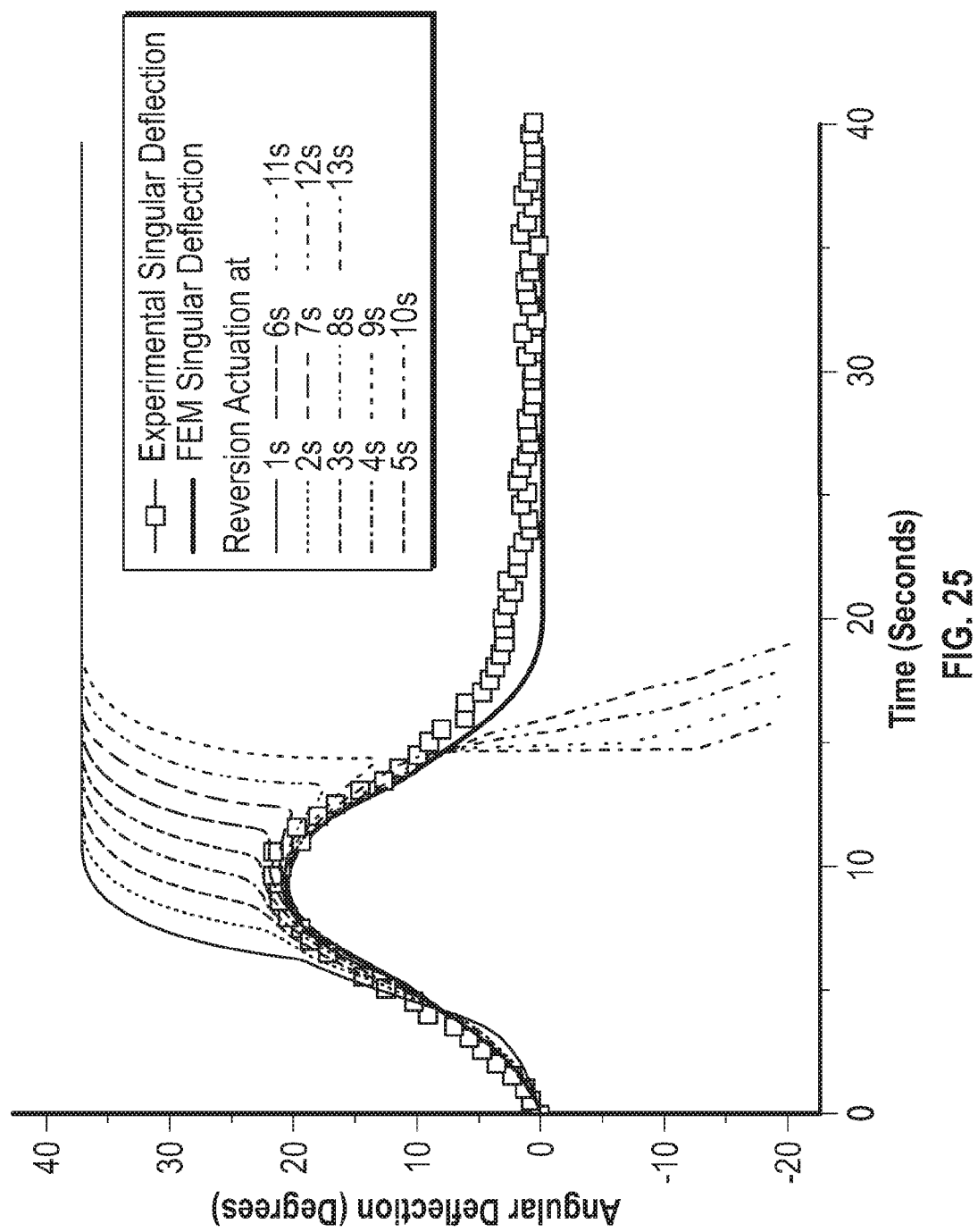
FIG. 25 is a plot of angular deflection versus time for an active needle prototype in a hypothetical case with two additional actuators implemented to promote recovery.

Finite element modeling was further performed to predict response of an active needle prototype equipped with two additional shape memory alloy actuators (i.e., for a total of three shape memory alloy actuators) for recovery purposes. A first shape memory alloy actuator was heated for the first 10 seconds for a complete phase transformation, and then started to cool down to room temperature. A maximum of 22 degrees of deflection was found with full actuation of the first shape memory alloy actuator. The studies consist of actuation of the second and third shape memory alloy actuator at various stages of during, or after, heating and cooling. The finite element modeling could predict the single actuator response with reasonable accuracy. FIG. 25 is a plot of angular deflection versus time for an active needle prototype in a hypothetical case with two additional actuators implemented to promote recovery. It could also be seen that with additional actuators, the recovery could be achieved when the first actuator is cooled down to partial contraction. It was seen that only after 5 seconds of cooling the main actuator, the opposing actuators could recover the shape of the active needle. Any actuation prior to 15 seconds resulted in additional deflection in the direction of first actuation.

Figure 26:
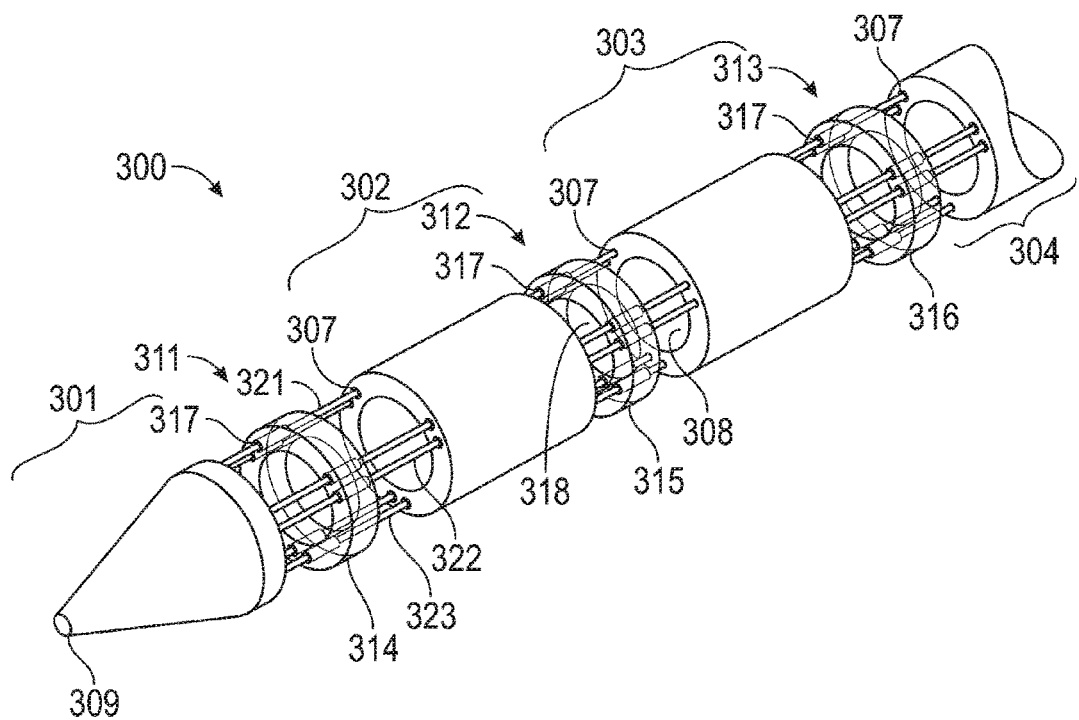
FIG. 26 is an exploded perspective view of a steerable surgical device according to an embodiment including shape memory alloy wire elements extending through longitudinal bores defined in tubular elements and joint elements of the steerable surgical device.
Figure 27:
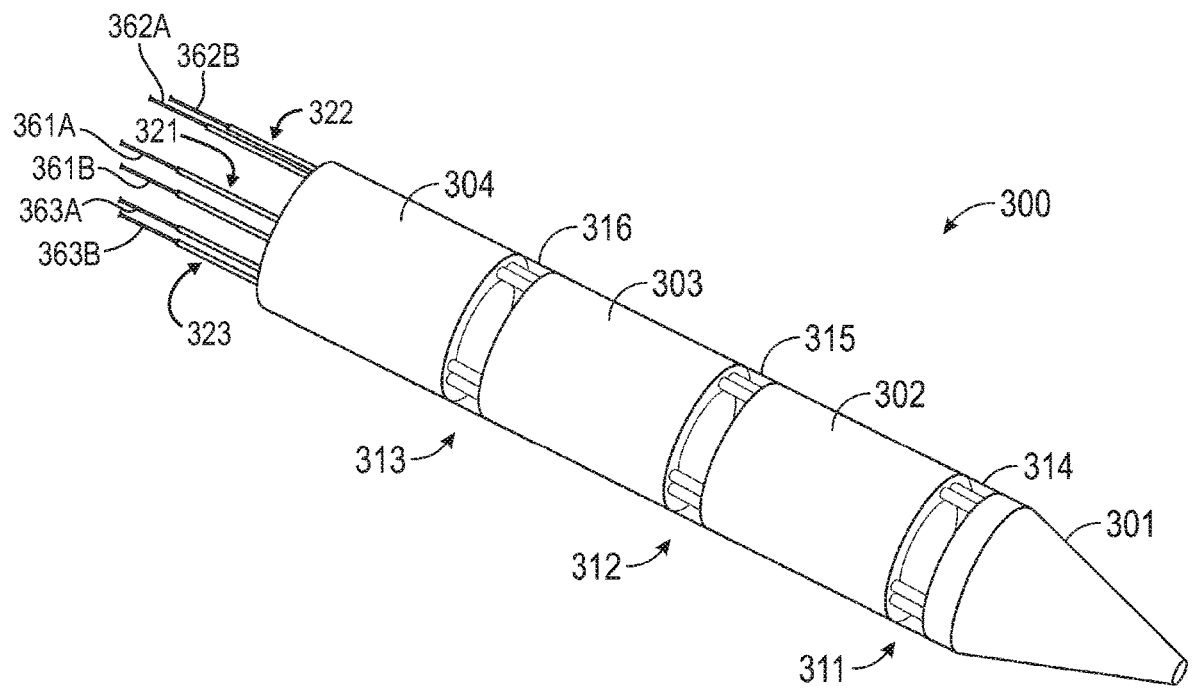
FIG. 27 is a perspective view of the steerable surgical device of FIG. 26 in an assembled state, with first and second ends of each shape memory alloy wire element being connected to a first electrical conductor and a second electrical conductor.
Figure 28:
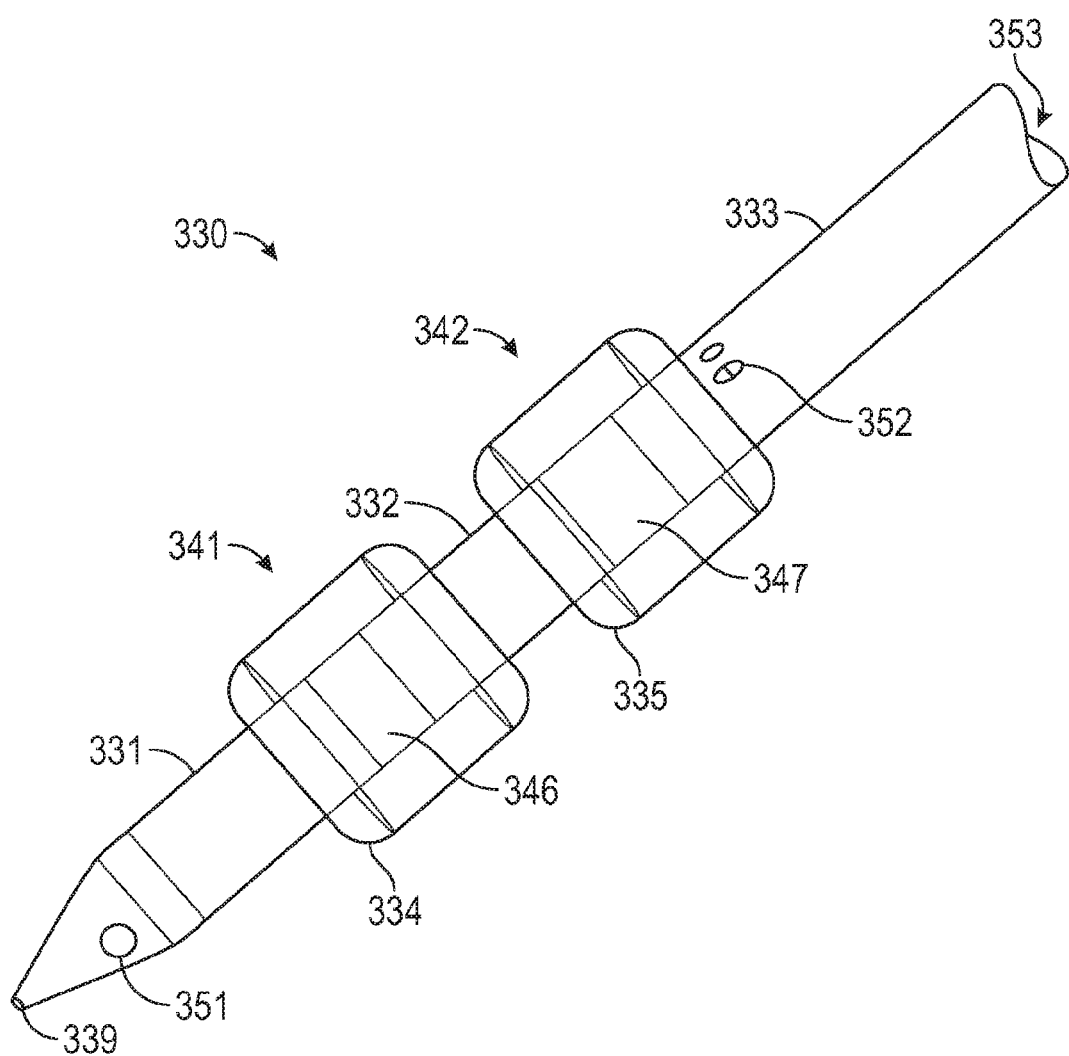
FIG. 28 is a perspective view of a steerable surgical device according to an embodiment including shape memory alloy wire elements extending through longitudinal bores defined in tubular elements, and increased diameter flexible collars arranged between tubular elements.

Additional steerable surgical device embodiments are shown in FIGS. 26-28. FIG. 26 is an exploded perspective view of a steerable surgical device 300 according to an embodiment including shape memory alloy wire elements 321-323 extending through longitudinal bores 307 defined in at least some tubular elements 302-304, and extending through longitudinal bores 317 defined in flexible elements 314-316 of the steerable surgical device 300. The steerable surgical device 300 includes first through fourth tubular elements 301-304, with the first tubular element including a needle tip 309 and having a substantially conical shape. Each flexible element 314-316 is positioned between, and forms a joint 311-313 between, a different pair of tubular elements 301-304. Each tubular element 301-303 may include an interior cavity 308, and each flexible element 314-316 likewise may include an interior cavity 318 such that the flexible elements 314-316 may be substantially annular in shape. As shown in FIG. 26, the tubular elements 302-304 each include three closely-spaced pairs of longitudinal bores 307, with a center of each pair of longitudinal bores 307 being about 120 degrees apart from a center of each other pair of longitudinal bores 307. Likewise, the flexible elements 314-316 each include three closely-spaced pairs of longitudinal bores 317, with a center of each pair of longitudinal bores 317 being about 120 degrees apart from a center of each other pair of longitudinal bores 317 defined through the flexible elements 314-316. The respective bores 307, 317 defined in the tubular elements 302-304 and defined in the flexible elements 314-316 are configured to permit the passage of shape memory alloy wire elements 321-323. Providing shape memory alloy wire actuators complete enclosed inside the steerable surgical device 300 (e.g., within bores 307, 317 defined in the tubular elements 302-304 and defined in the flexible elements 314-316) avoids contact between the shape memory alloy wire actuators and tissue, thereby preventing the heating of shape memory alloy actuators from causing tissue damage when the steerable surgical device 300 is used inside a patient's body.

In certain embodiments, a first end of each shape memory alloy wire element 321-323 may be inserted (in a direction generally toward the needle tip 309) through a longitudinal bore 307 defined in the fourth tubular element 304, through a longitudinal bore 317 defined in the third flexible element 316, through a longitudinal bore 307 defined in the third tubular element 303, through a longitudinal bore 317 defined in the second flexible element 315, through a longitudinal bore 307 defined in the second tubular element 302, through a longitudinal bore 317 defined in the first flexible element 314, and into an interior of the first tubular element 301 to be received by an anchor (e.g., loop, post, or the like), and then returned in reverse order (away from the needle tip 309) through a paired (closely spaced) longitudinal bore 317 defined in the first flexible element 314, through a paired (closely spaced) longitudinal bore 307 defined in the second tubular element 302, and so on, until the respective shape memory alloy wire element 321-323 exits the fourth tubular element 304. In this manner, each pair of longitudinal bores 307 in the tubular elements 302-304 and each pair of longitudinal bores 317 in the flexible elements 314-316 receives a single shape memory wire element 321-323, such that first and second ends of each shape memory wire element 321-323 may be accessible at an end of the steerable surgical device 300 distal from the needle tip 309 (i.e., as shown in FIG. 27). Actuation of a single shape memory wire element 321-323 may cause each joint 311-313 to pivot along one deflection plane. Individually controllable actuation of the shape memory wire elements 321-323 may permit the pivotal movement of the needle tip 309 along at least three planes, such that three-dimensional pivotal movement of the needle tip 209 is enabled.

FIG. 27 is a perspective view of the steerable surgical device 300 of FIG. 26 in an assembled state, showing the flexible elements 311-313 arranged between and in contact with different pairs of the tubular elements 301 304. FIG. 27 further shows both (i.e., first and second) ends of each of three shape memory alloy wire elements 321-323 extending outward beyond the fourth tubular element 304, with a first end of each shape memory alloy wire element 321-323 being coupled with a corresponding first electrical conductor 361A, 362A, 363A, and with a second end of each shape memory alloy wire element 321-323 being coupled with a corresponding second electrical conductor 361B, 362B, 363B.

Elements of the steerable surgical device 300 of FIGS. 26-27 may be produced by any suitable means, including extrusion, 3D printing, or the like. In certain embodiments, the tubular elements 301-304 may comprise polymeric material (optionally reinforced) such as fluoropolymers, polyolefins, polyamides, or the like. A 3D printed 4:1 scaled prototype of a steerable surgical device consistent with the design of FIGS. 26-27 was produced with a stereolithographic 3D printer (PolyJet) having a resolution of 0.0508 mm along the X and Y directions, and a resolution of 0.203 mm in the Z direction. The tubular elements were printed with Somos® PerFORM material (Proto Labs, Maple Plain, Minn.) having a tensile strength of 80 MPa and a heat deflection temperature (HDT) of 268° C., and the flexible elements were printed with digital photopolymer (Proto Labs, Maple Plain, Minn.), a clear material having hardness of Shore A 40, a tensile strength of 3.0 to 4.0 MPa, and a tensile tear strength of 6.0-8.0 kg/cm.

FIG. 28 is a perspective view of a steerable surgical device 330 according to another embodiment (similar to FIGS. 26-27) including shape memory alloy wire elements (not shown) extending through longitudinal guide elements (e.g., bores or channels, not shown) defined within the tubular elements 331-333. However, the steerable surgical device 330 of FIG. 28 includes increased diameter flexible collars 334, 335 arranged between, and serving as joints 341, 342 between, respective pairs of tubular elements 331-333. In certain embodiments, each flexible collar 334, 335 may comprise silicone or another suitably flexible and biocompatible material, and includes rounded edges to facilitate passage through body tissues. The increased diameter material of the flexible collars 334, 335 may exert a biasing or restoring force tending to collinearly align the tubular elements 331-333 when shape memory alloy wire elements within the steerable surgical device 330 are in an unactuated state. Dimensions, shapes, and elastic moduli of the flexible collars may be selected to obtain a desired balance of flexibility, restoring force, and ease passage through tissues or organs of a patient. The first tubular element 331 includes a needle tip 339 and a functional feature 351 (e.g., opening for ingress of biopsy tissue or egress of a therapeutic agent, or a sensor). A second tubular element 332 is arranged between first and second flexible collars 334, 335, with the second flexible collar 335 being arranged between the second tubular element 332 and a third tubular element 333. Each tubular element 331-333 may include an internal cavity 353. The third tubular element 333 may include an additional functional element 352 (e.g., sensor, etc.). Each flexible collar 334, 335 has an increased width relative to each tubular element 331-333. Each flexible collar 334, 335 further defines a cavity 346, 347 permitting passage between cavities 353 defined in the different tubular elements 331-

333. Although not shown, it is to be understood that multiple shape memory alloy wire elements may be arranged within the tubular elements 331-333 and the joints 341, 342 to effectuate pivotal movement between the tubular elements 331-333 at the joints 341, 342, thereby permitting the needle tip 339 to be actively steered in different directions (e.g., along at least two or at least three non-parallel planes).

In certain embodiments, longitudinal bores defined in tubular elements and defined joint elements of a steerable surgical device may be used to permit passage of not only one or more shape memory alloy wire elements, but also to contain a coolant medium (e.g., fluid such as liquid or gas) to enhance heat transfer and permit heated shape memory alloy wire elements to cool more rapidly after actuation. In certain embodiments, such longitudinal bores may be permit coolant medium to flow therethrough in direct contact with shape memory alloy wire elements, with such flow optionally being motivated by a positive pressure pump and/or a vacuum pump. In certain embodiments, a coolant medium may comprise a substantially inert gas (e.g., nitrogen gas, carbon dioxide gas, etc.) or a liquid such as water or water-based solutions such as saline solution. Other coolant media may be used.

A method for fabricating at least a portion of a steerable surgical device (e.g., according to FIGS. 1A-1C) may include multiple steps, as described hereinafter. One step includes inserting a first shape memory alloy wire element into (i) at least one longitudinal slot of a first longitudinal guide body of a first semi-tubular portion of a first tubular element and (ii) at least one longitudinal slot of a first longitudinal guide body of a first semi-tubular portion of a second tubular element. Another step includes joining the first semi-tubular portion of the first tubular element with the first semi-tubular portion of the second tubular element using a first semi-tubular joint portion. Another step includes pre-tensioning the first shape memory alloy wire element, and affixing end portions of the first shape memory alloy wire element to end portions of one or more of (a) the first longitudinal guide body of the first semi-tubular portion of the first tubular element or (b) the second longitudinal guide body of the first semi-tubular portion of the second tubular element.

Another step includes inserting a second shape memory alloy wire element into (i) at least one longitudinal slot of a second longitudinal guide body of a second semi-tubular portion of the first tubular element and (ii) at least one longitudinal slot of a second longitudinal guide body of a second semi-tubular portion of the second tubular element. Another step includes joining the second semi-tubular portion of the first tubular element with the second semi-tubular portion of the second tubular element using a second semi-tubular joint portion. Another step includes pre-tensioning the second shape memory alloy wire element, and affixing end portions of the second shape memory alloy wire element to end portions of one or more of (a) the second longitudinal guide body of the second semi-tubular portion of the first tubular element or (b) the second longitudinal guide body of the second semi-tubular portion of the second tubular element.

Another step includes mating the first semi-tubular portion of the first tubular element with the second semi-tubular portion of the first tubular element, mating the first semi-tubular joint portion with the second semi-tubular joint portion, and mating the first semi-tubular portion of the second tubular element with the second semi-tubular portion of the second tubular element.

It is contemplated that any or more features or characteristics of any one or more embodiments disclosed herein may be combined with those of other embodiments, unless specifically indicated to the contrary herein.

Those skilled in the art will recognize improvements and modifications to the exemplary embodiments of the present disclosure. All such improvements and modifications are considered within the scope of the concepts disclosed herein and the claims that follow.

What is claimed is:

1. A steerable surgical device comprising:
   a first tubular element comprising a first plurality of anchor points, including anchor points circumferentially spaced from one another;
   a second tubular element comprising a second plurality of anchor points, including anchor points circumferentially spaced from one another;
   a first joint arranged between, and configured to allow pivotal movement between, the first tubular element and the second tubular element; and
   a plurality of shape memory alloy wire elements extending across or through the first joint, attached to the first plurality of anchor points, and attached to the second plurality of anchor points;
   wherein at least some shape memory alloy wire elements of the plurality of shape memory alloy wire elements are independently actuatable to effectuate pivotal movement between the first tubular element and the second tubular element; and
   wherein each shape memory alloy wire element of the plurality of shape memory alloy wire elements comprises a first end in conductive electrical communication with a first electrical conductor and a second end in conductive electrical communication with a second electrical conductor.

2. The steerable surgical device of claim 1, wherein the at least some shape memory alloy wire elements are configured to permit adjustment of pivot angle between the first tubular element and the second tubular element along at least two non-parallel planes.

3. The steerable surgical device of claim 1, wherein individual shape memory alloy wire elements of the plurality of shape memory alloy wire elements are configured to contract responsive to application of an electrical current thereto to cause pivotal movement between the first tubular element and the second tubular element.

4. The steerable surgical device of claim 1, wherein each shape memory alloy wire element of the plurality of shape memory alloy wire elements is in conductive electrical communication with at least one electrical conductor.

5. The steerable surgical device of claim 1, wherein the first plurality of anchor points is interior to the first tubular element and the second plurality of anchor points is interior to the second tubular element.

6. The steerable surgical device of claim 1, wherein at least some shape memory alloy wire elements of the plurality of shape memory alloy wire elements are pretensioned between at least some anchor points of the first plurality of anchor points and at least some anchor points of the second plurality of anchor points.

7. The steerable surgical device of claim 6, wherein the at least some shape memory alloy wire elements each comprise a pretensioning stress value in a range of from about 100 MPa to about 200 Mpa.

8. The steerable surgical device of claim 1, wherein each shape memory alloy wire element of the plurality of shape memory alloy wire elements comprises a diameter in a range of from about 0.1 mm to about 0.2 mm.

9. The steerable surgical device of claim 1, wherein:
each shape memory alloy wire element of the plurality of shape memory alloy wire elements comprises a first end, a second end, a first attachment point proximate the first end, a second attachment point proximate the second end, and an intermediate point arranged between the first and second ends; and
the first attachment point and the second attachment point of each shape memory alloy wire element are attached to at least one anchor point of the first plurality of anchor points, and the intermediate point of each shape memory alloy wire element is attached to at least one anchor point of the second plurality of anchor points.

10. The steerable surgical device of claim 1, wherein:
at least one anchor point of the first plurality of anchor points is circumferentially spaced from at least one other anchor point of the first plurality of anchor points by a distance equal to an arc length defined by a first angle of at least 90 degrees when a vertex of the first angle coincides with a center of the first tubular element; and
at least one anchor point of the second plurality of anchor points is circumferentially spaced from at least one other anchor point of the second plurality of anchor points by a distance equal to arc length defined by a second angle of at least 90 degrees when of the second angle coincides with the center of the second tubular element.

11. The steerable surgical device of claim 1, wherein the plurality of shape memory alloy wire elements comprises first, second, and third shape memory alloy wire elements, with each of the first, second, and third shape memory alloy wire elements being independently controllable and circumferentially spaced apart from each other of the first, second, and third shape memory alloy wire elements to enable three-dimensional pivotal movement of the first tubular element relative to the second tubular element.

12. The steerable surgical device of claim 11, wherein at least portions of the first, second, and third shape memory alloy wire elements are arranged proximate to an interior surface of the first tubular element.

13. The steerable surgical device of claim 11, wherein at least portions of the first, second, and third shape memory alloy wire elements extend in a longitudinal direction through a wall of the first tubular element and through a wall of the second tubular element.

14. The steerable surgical device of claim 11, wherein each of the first, second, and third shape memory alloy wire elements is pretensioned.

15. The steerable surgical device of claim 14, wherein the first tubular element is biased toward a linear alignment with the second tubular element by pretensioning of the first, second, and third shape memory alloy wire elements.

16. The steerable surgical device of claim 1, wherein:
the first tubular element comprises a first semi-tubular portion extending in a longitudinal direction and a second semi-tubular portion extending in the longitudinal direction, with the second semi-tubular portion being configured to mate with the first semi-tubular portion; and
the first plurality of anchor points comprises a primary anchor point positioned in the first semi-tubular portion, and comprises secondary and tertiary anchor points positioned in the second semi-tubular portion.

17. The steerable surgical device of claim 1, wherein the first joint comprises a stiffness that is less than a stiffness of the first tubular element and less than a stiffness of the second tubular element.

18. The steerable surgical device of claim 1, wherein the first joint comprises a flexible sleeve.

19. The steerable surgical device of claim 1, further comprising:
a third tubular element arranged between the first tubular element and the first joint; and
a second joint arranged between, and configured to allow pivotal movement between, the first tubular element and the third tubular element;
wherein the plurality of shape memory alloy wire elements further extend across or through the second joint; and
wherein at least some shape memory alloy wire elements of the plurality of shape memory alloy wire elements are independently actuatable to effectuate pivotal movement between the first tubular element and the second tubular element, and pivotal movement between the first tubular element and the third tubular element.

20. The steerable surgical device of claim 1, wherein:
each of the first tubular element and the second tubular element comprises a plurality of longitudinal guide structures each configured to receive at least one shape memory alloy wire element of the plurality of shape memory alloy wire elements.

21. The steerable surgical device of claim 20, wherein each longitudinal guide structure of the plurality of longitudinal guide structures comprises a guide body defining at least one longitudinal slot arranged proximate to an internal wall of either the first tubular element or the second tubular element.

22. The steerable surgical device of claim 20, wherein each longitudinal guide structure of the plurality of longitudinal guide structures defines a longitudinal bore defined in a wall of either the first tubular element or the second tubular element.

23. The steerable surgical device of claim 20, wherein an anchor point of the first plurality of anchor points is arranged proximate to one end of each longitudinal guide structure, an anchor point of the second plurality of anchor points is arranged proximate to an opposing end of each longitudinal guide structure, and each shape memory alloy wire element of the plurality of shape memory alloy wire elements is configured for slidable movement within a different longitudinal guide structure of the plurality of longitudinal guide structures.

24. The steerable surgical device of claim 1, wherein separate actuation of the shape memory alloy wire elements is configured to permit adjustment of pivot angle between the first tubular element and the second tubular element along at least three non-parallel planes.

25. The steerable surgical device of claim 1, wherein the first tubular element comprises a needle tip.

26. The steerable surgical device of claim 1, wherein the steerable surgical device comprises at least one of a catheter, a cannula, or a guidewire.

27. The steerable surgical device of claim 1, wherein the plurality of shape memory alloy wire elements comprise a thermally responsive shape memory alloy wire element.

28. The steerable surgical device of claim 1, being configured for positioning and deployment of an implantable mitral valve repair device.

29. A steerable surgical device comprising:
a first tubular element comprising a first plurality of anchor points, including anchor points circumferentially spaced from one another;
a second tubular element comprising a second plurality of anchor points, including anchor points circumferentially spaced from one another;
a first joint arranged between, and configured to allow pivotal movement between, the first tubular element and the second tubular element; and
a plurality of shape memory alloy wire elements extending across or through the first joint, attached to the first plurality of anchor points, and attached to the second plurality of anchor points;
wherein each shape memory alloy wire element of the plurality of shape memory alloy wire elements comprises a first end, a second end, a first attachment point proximate the first end, a second attachment point proximate the second end, and an intermediate point arranged between the first and second ends;
wherein the first attachment point and the second attachment point of each shape memory alloy wire element are attached to at least one anchor point of the first plurality of anchor points, and the intermediate point of each shape memory alloy wire element is attached to at least one anchor point of the second plurality of anchor points; and
wherein at least some shape memory alloy wire elements of the plurality of shape memory alloy wire elements are independently actuatable to effectuate pivotal movement between the first tubular element and the second tubular element.

30. The steerable surgical device of claim 29, wherein:
the first tubular element comprises a first plurality of longitudinal guide structures, wherein at least one longitudinal guide structure of the first plurality of longitudinal guide structures is circumferentially spaced from at least one other longitudinal guide structure of the first plurality of longitudinal guide structures;
the second tubular element comprises a second plurality of longitudinal guide structures, wherein at least one longitudinal guide structure of the second plurality of longitudinal guide structures is circumferentially spaced from at least one other longitudinal guide structure of the second plurality of longitudinal guide structures; and
the plurality of shape memory wire elements extends through the first plurality of longitudinal guide structures, extends across or through the first joint, and extends through the second plurality of longitudinal guide structures.

31. A steerable surgical device comprising:
a first tubular element comprising a first plurality of anchor points, including anchor points circumferentially spaced from one another, wherein the first tubular element comprises a first semi-tubular portion extending in a longitudinal direction and a second semi-tubular portion extending in the longitudinal direction, with the second semi-tubular portion being configured to mate with the first semi-tubular portion;
a second tubular element comprising a second plurality of anchor points, including anchor points circumferentially spaced from one another;
a first joint arranged between, and configured to allow pivotal movement between, the first tubular element and the second tubular element; and
a plurality of shape memory alloy wire elements extending across or through the first joint, attached to the first plurality of anchor points, and attached to the second plurality of anchor points;
wherein the first plurality of anchor points comprises a primary anchor point positioned in the first semi-tubular portion, and comprises secondary and tertiary anchor points positioned in the second semi-tubular portion; and
wherein at least some shape memory alloy wire elements of the plurality of shape memory alloy wire elements are independently actuatable to effectuate pivotal movement between the first tubular element and the second tubular element.

32. A steerable surgical device comprising:
a first tubular element comprising a first plurality of anchor points, including anchor points circumferentially spaced from one another;
a second tubular element comprising a second plurality of anchor points, including anchor points circumferentially spaced from one another;
a first joint arranged between, and configured to allow pivotal movement between, the first tubular element and the second tubular element; and
a plurality of shape memory alloy wire elements extending across or through the first joint, attached to the first plurality of anchor points, and attached to the second plurality of anchor points;
wherein each shape memory alloy wire element of the plurality of shape memory alloy wire elements comprises a first end, a second end, a first attachment point proximate the first end, a second attachment point proximate the second end, and an intermediate point arranged between the first and second ends;
wherein the first attachment point and the second attachment point of each shape memory alloy wire element are attached to at least one anchor point of the first plurality of anchor points, and the intermediate point of each shape memory alloy wire element is attached to at least one anchor point of the second plurality of anchor points; and
wherein at least some shape memory alloy wire elements of the plurality of shape memory alloy wire elements are independently actuatable to effectuate pivotal movement between the first tubular element and the second tubular element.

33. The steerable surgical device of claim 32, wherein the first joint comprises a first semi-tubular joint portion and comprises a second semi-tubular joint portion configured to mate with the first semi-tubular joint portion.

34. The steerable surgical device of claim 32, wherein the first semi-tubular portion comprises a first half-tubular portion, and the second semi-tubular portion comprises a second half-tubular portion.

* * * * *